(12) United States Patent
Berg et al.

(10) Patent No.: US 7,951,568 B2
(45) Date of Patent: May 31, 2011

(54) BI-DIRECTIONAL SELECTION MARKERS WITH IMPROVED ACTIVITY

(75) Inventors: Marco Alexander van den Berg, Poeldijk (NL); Roelof Ary Lans Bovenberg, Rotterdam (NL)

(73) Assignee: DSM IP Assets B.V., Heerlen (NL)

( * ) Notice: Subject to any disclaimer, the term of this patent is extended or adjusted under 35 U.S.C. 154(b) by 247 days.

(21) Appl. No.: 12/226,282

(22) PCT Filed: Apr. 12, 2007

(86) PCT No.: PCT/EP2007/053549
§ 371 (c)(1), (2), (4) Date: Oct. 14, 2008

(87) PCT Pub. No.: WO2007/118836
PCT Pub. Date: Oct. 25, 2007

(65) Prior Publication Data
US 2009/0246826 A1 Oct. 1, 2009

(30) Foreign Application Priority Data
Apr. 13, 2006 (EP) .................................... 06112618

(51) Int. Cl.
C12N 9/00 (2006.01)
C07H 21/04 (2006.01)
(52) U.S. Cl. ....................................... 435/183; 536/23.2
(58) Field of Classification Search .................. 435/183; 536/23.2
See application file for complete search history.

(56) References Cited

U.S. PATENT DOCUMENTS

| 6,548,285 B1 | 4/2003 | Swinkels et al. |
| 2008/0070277 A1 | 3/2008 | Sagt et al. |

FOREIGN PATENT DOCUMENTS

| WO | 97/06261 | 2/1997 |
| WO | 2006/040358 | 4/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS, 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Corrick et al. "The nucleotide of the amdS gene of *Aspergillus nidulans* and the molecular characterization of 5' mutations" Gene 53:63-71 (1987).
Debets et al. "Genetic analysis of amdS transformants of *Aspergillus niger* and their use in chromosome mapping" Mol. Gen. Genet. 222:284-290 (1990).
Machida et al. "Amidases" Database Accession No. Q2PIS7(2006).
International Search Report for PCT/EP2007/053549 mailed Sep. 21, 2007.

\* cited by examiner

*Primary Examiner* — Ganapathirama Raghu
(74) *Attorney, Agent, or Firm* — Nixon & Vanderhye P.C.

(57) ABSTRACT

The present invention discloses a polypeptide selected from the group consisting of: a polypeptide having an amino acid sequence according to SEQ ID NO 3, a polypeptide having an amino acid sequence according to SEQ ID NO 6, a polypeptide having an amino acid that is substantially homologous to the sequence of SEQ ID NO 3 and a polypeptide having an amino acid that is substantially homologous to the sequence of SEQ ID NO 6, the polypeptide displaying acetamidase activity and providing a reverse selection on fluoroacetamide with an efficiency of at least 95%, preferably at least 96%, more preferably at least 97%, more preferably at least 98%, more preferably at least 99%, most preferably 100%. The gene encoding the polypeptide of the invention is used as an efficient bi-directional selection marker in the construction of selection marker free strains, in particular for processes for the production of a compound of interest.

1 Claim, 8 Drawing Sheets

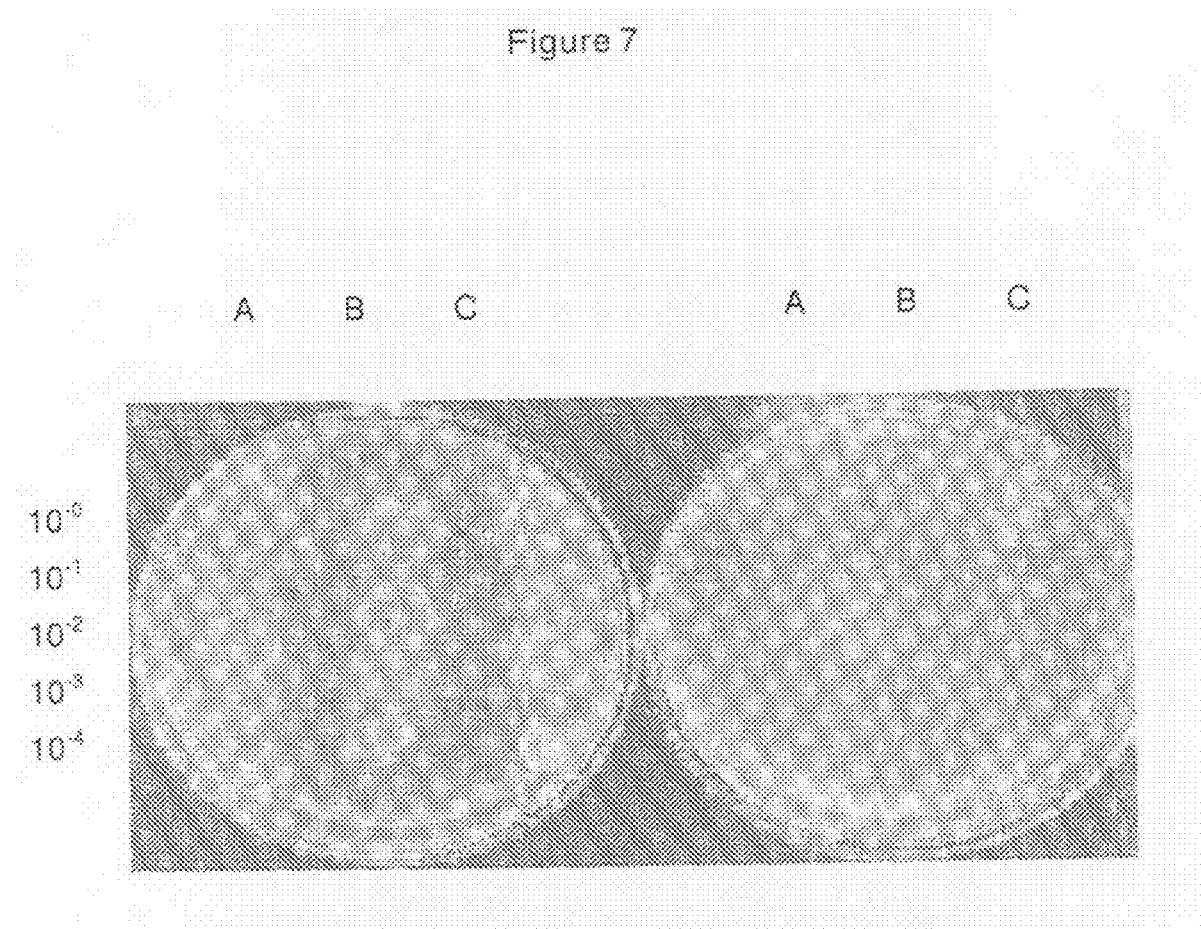

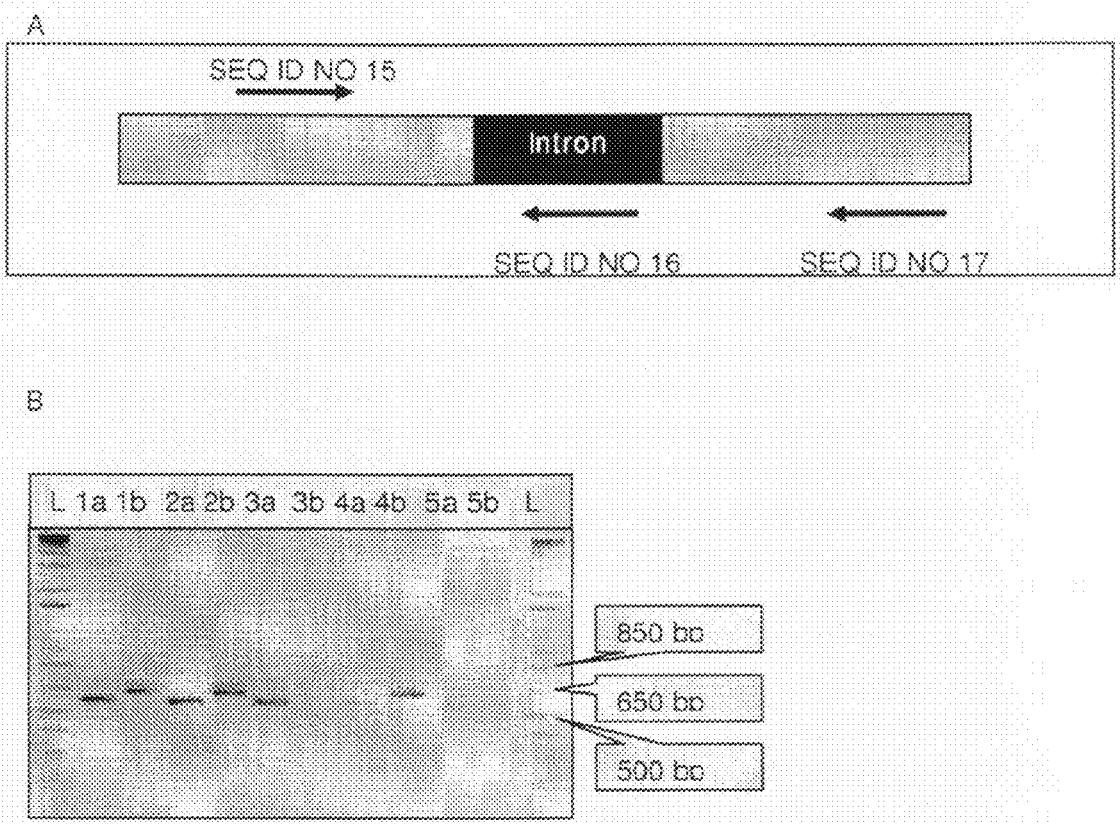

SEQUENCE LISTING

```
<160> NUMBER OF SEQ ID NOS: 17

<210> SEQ ID NO 1
<211> LENGTH: 2542
<212> TYPE: DNA
<213> ORGANISM: Penicillium chrysogenum

<400> SEQUENCE: 1
```

-continued

```
agatggggaa tccagatctc aggaacgtga ttctttccct ggtccaaaca tggacaactt      60
tctatagtgc catactcaag cacagatgca gtcatgctgt tccaatgcgt cctgtcaaat     120
tccccaatga ggcatttcct cttgagaata gtgtgcggat tgtatttcca cgaggatgat     180
aatctgatcg agataacaac cagcccttag acgaatcaat tgcacttaaa tagagcgact     240
aatatggaca tctctgcaat actccacatg aaagaccgta acgcgcaaag ggtgtgggcg     300
ataagctagc ctccaactgt tcgtgttca atgaccccaa taaccccgca ccactgtatg      360
tacactttgt ggaagtctcc tacaaccct cgacatatct agttgaaaat gactggcaca     420
tcctggaaac tgaaggcga agccaaacgc cagtcaattt taaatgctat tcccgagaaa     480
tggcgactgg aatctcctgt ccctcccgct acagaactac gagatgttac aggggattat     540
attcgacaat acctcaccga gcatgagatc actatcacag agacagatgc cgtagacatt     600
gtggcgcaga catctacagg ccgctggtca gccctggaag tgacagaagc cttctgtcac     660
cgggctgcat tggctcacca actcgtacgt ttatataccg gcagcgcgtg cacaagaatg     720
catcgagctc agacaaccaa ataaaactaa ccaatcaccg aaccctaggt caactgtctg     780
cacgaggtat tcttcgaagc cgcaattcaa gatgccaaac agcaagacga atacttcgca     840
aaacacaaaa ccccgatagg acctctacat ggcctaccag tgagtctaaa agaccaattt     900
cacgcgaaag gcgtcgaaac cacaatgggc tacgtaggct ggataaacac cttccaaggc     960
cgacagaacg acccgcgcag cggcacagaa gaaagcgaac tcgtccgcgc actacgcaat    1020
ctcggtgccg tcctgtactg caagaccagc gtgccagcca ccctgatggt cggcgaaacc    1080
atgaacaaca tcatcggcta cacctggaac cccaagaacc gcctgctatc cagtggcggc    1140
agctctggcg gcgagggcgc cctaattgcg ctccgcggct cgcctgctgg cttcggcact    1200
gatatcggag gtagtgtgcg catcccagct gggtttaatt ccctgtatgg gattcgtcct    1260
tcggcaggta ggattcctta ccaaggtgct gcgaactcgt tggatgggca ggggtctata    1320
ttgtctgtta ttgggccgat tgcgccgagt gcgaggtctt tgacgttctt gttcaaggct    1380
gttcttagcc aggagccttg gttgcatgat ccacttgcgt tggagctgcc gtggagggat    1440
gaggttgttc gggagaccag ggctttgatt gcgaagggtc gagctgggtc gccgacgctt    1500
gcgttcggca ttatgaaata cgatggtatg gcacttgttc atccgcctat tgcgcggggg    1560
ctcaggattg ttgagaaaac gctacggcgg ttgggtcatc gggttgttga gtggacgcct    1620
ccttctcact caattgccaa tgaactactt gtatgtacct gtgcgtgaaa tccggcacgt    1680
tgctgacttg tcgcagggta aaatattcaa catggatggc ggcgcagatg tgaaatatca    1740
tctgggtctg tctggagaac ctcaagcccc ggaaatagtc tgcaacgaga atggtattca    1800
gatgacagca tctgagattg cggcgctcaa tgttgcgaag cgtgagtatc agaaacagta    1860
tatggactac tggcatagca cagccgaggt gacaggcacg gggcgtcctg ttgatgcgct    1920
attttgccca ttggcacctc atgcggcagt tattcccggc gaattcaagt ctgtgggata    1980
tactggattt gtgaatgtgc ttgactatac tagccttgcg attccagtca catttgcgga    2040
taagaatatc gatgtgcgct cggccaatga gtctgtggat gattctgagc atattcagtg    2100
ggattgtgcg tttcccccat accttcactc tcgtggttcc atactgatcg ctatatagac    2160
gatgccgagg cctacgatgg ggccccgtg ggagtgcaat tggtaggcag gaggttgcag     2220
gaagagaaga tgttgactct agctgagtat ttcgaagaag agattgctcg agacacgaaa    2280
gagagagcct gagtctacaa taccagactc atcacgttac tgtaacagag catgtgcgca    2340
ttgattacga ttaagatgaa ccacttgcat ttcgtatggg tataataaat gaccgtgcta    2400
```

-continued

```
ttctctacca agaagagtgg atctagaaac ggagagagca gaccaagcgt actgcctaca      2460
gccaatgcag aggataaatc atagctccca gataccttgg cttatccggt ccttcttcta      2520
cagatattat atacccaaaa ag                                               2542

<210> SEQ ID NO 2
<211> LENGTH: 1701
<212> TYPE: DNA
<213> ORGANISM: Penicillium chrysogenum
<220> FEATURE:
<221> NAME/KEY: CDS
<222> LOCATION: (1)..(1701)

<400> SEQUENCE: 2 atg act ggc aca tcc tgg aaa ctg aaa ggc gaa gcc aaa cgc cag tca        48
Met Thr Gly Thr Ser Trp Lys Leu Lys Gly Glu Ala Lys Arg Gln Ser
1               5                  10                  15 att tta aat gct att ccc gag aaa tgg cga ctg gaa tct cct gtc cct        96
Ile Leu Asn Ala Ile Pro Glu Lys Trp Arg Leu Glu Ser Pro Val Pro
            20                  25                  30 ccc gct aca gaa cta cga gat gtt aca ggg gat tat att cga caa tac       144
Pro Ala Thr Glu Leu Arg Asp Val Thr Gly Asp Tyr Ile Arg Gln Tyr
        35                  40                  45 ctc acc gag cat gag atc act atc aca gag aca gat gcc gta gac att       192
Leu Thr Glu His Glu Ile Thr Ile Thr Glu Thr Asp Ala Val Asp Ile
    50                  55                  60 gtg gcg cag aca tct aca ggc cgc tgg tca gcc ctg gaa gtg aca gaa       240
Val Ala Gln Thr Ser Thr Gly Arg Trp Ser Ala Leu Glu Val Thr Glu
65                  70                  75                  80 gcc ttc tgt cac cgg gct gca ttg gct cac caa ctc gtc aac tgt ctg       288
Ala Phe Cys His Arg Ala Ala Leu Ala His Gln Leu Val Asn Cys Leu
                85                  90                  95 cac gag gta ttc ttc gaa gcc gca att caa gat gcc aaa cag caa gac       336
His Glu Val Phe Phe Glu Ala Ala Ile Gln Asp Ala Lys Gln Gln Asp
            100                 105                 110 gaa tac ttc gca aaa cac aaa acc ccg ata gga cct cta cat ggc cta       384
Glu Tyr Phe Ala Lys His Lys Thr Pro Ile Gly Pro Leu His Gly Leu
        115                 120                 125 cca gtg agt cta aaa gac caa ttt cac gcg aaa ggc gtc gaa acc aca       432
Pro Val Ser Leu Lys Asp Gln Phe His Ala Lys Gly Val Glu Thr Thr
    130                 135                 140 atg ggc tac gta ggc tgg ata aac acc ttc caa ggc cga cag aac gac       480
Met Gly Tyr Val Gly Trp Ile Asn Thr Phe Gln Gly Arg Gln Asn Asp
145                 150                 155                 160 ccg cgc agc ggc aca gaa gaa agc gaa ctc gtc cgc gca cta cgc aat       528
Pro Arg Ser Gly Thr Glu Glu Ser Glu Leu Val Arg Ala Leu Arg Asn
                165                 170                 175 ctc ggt gcc gtc ctg tac tgc aag acc agc gtg cca gcc acc ctg atg       576
Leu Gly Ala Val Leu Tyr Cys Lys Thr Ser Val Pro Ala Thr Leu Met
            180                 185                 190 gtc ggc gaa acc atg aac aac atc atc ggc tac acc tgg aac ccc aag       624
Val Gly Glu Thr Met Asn Asn Ile Ile Gly Tyr Thr Trp Asn Pro Lys
        195                 200                 205 aac cgc ctg cta tcc agt ggc ggc agc tct ggc ggc gag ggc gcc cta       672
Asn Arg Leu Leu Ser Ser Gly Gly Ser Ser Gly Gly Glu Gly Ala Leu
    210                 215                 220 att gcg ctc cgc ggc tcg cct gct ggc ttc ggc act gat atc gga ggt       720
Ile Ala Leu Arg Gly Ser Pro Ala Gly Phe Gly Thr Asp Ile Gly Gly
225                 230                 235                 240 agt gtg cgc atc cca gct ggg ttt aat tcc ctg tat ggg att cgt cct       768
Ser Val Arg Ile Pro Ala Gly Phe Asn Ser Leu Tyr Gly Ile Arg Pro
```

-continued

```
              245                 250                 255
tcg gca ggt agg att cct tac caa ggt gct gcg aac tcg ttg gat ggg    816
Ser Ala Gly Arg Ile Pro Tyr Gln Gly Ala Ala Asn Ser Leu Asp Gly
        260                 265                 270 cag ggg tct ata ttg tct gtt att ggg ccg att gcg ccg agt gcg agg    864
Gln Gly Ser Ile Leu Ser Val Ile Gly Pro Ile Ala Pro Ser Ala Arg
        275                 280                 285 tct ttg acg ttc ttg ttc aag gct gtt ctt agc cag gag cct tgg ttg    912
Ser Leu Thr Phe Leu Phe Lys Ala Val Leu Ser Gln Glu Pro Trp Leu
        290                 295                 300 cat gat cca ctt gcg ttg gag ctg ccg tgg agg gat gag gtt gtt cgg    960
His Asp Pro Leu Ala Leu Glu Leu Pro Trp Arg Asp Glu Val Val Arg
305                 310                 315                 320 gag acc agg gct ttg att gcg aag ggt cga gct ggg tcg ccg acg ctt   1008
Glu Thr Arg Ala Leu Ile Ala Lys Gly Arg Ala Gly Ser Pro Thr Leu
                325                 330                 335 gcg ttc ggc att atg aaa tac gat ggt atg gca ctt gtt cat ccg cct   1056
Ala Phe Gly Ile Met Lys Tyr Asp Gly Met Ala Leu Val His Pro Pro
                340                 345                 350 att gcg cgg ggg ctc agg att gtt gag aaa acg cta cgg cgg ttg ggt   1104
Ile Ala Arg Gly Leu Arg Ile Val Glu Lys Thr Leu Arg Arg Leu Gly
                355                 360                 365 cat cgg gtt gtt gag tgg acg cct cct tct cac tca att gcc aat gaa   1152
His Arg Val Val Glu Trp Thr Pro Pro Ser His Ser Ile Ala Asn Glu
370                 375                 380 cta ctt ggt aaa ata ttc aac atg gat ggc ggc gca gat gtg aaa tat   1200
Leu Leu Gly Lys Ile Phe Asn Met Asp Gly Gly Ala Asp Val Lys Tyr
385                 390                 395                 400 cat ctg ggt ctg tct gga gaa cct caa gcc ccg gaa ata gtc tgc aac   1248
His Leu Gly Leu Ser Gly Glu Pro Gln Ala Pro Glu Ile Val Cys Asn
                405                 410                 415 gag aat ggt att cag atg aca gca tct gag att gcg gcg ctc aat gtt   1296
Glu Asn Gly Ile Gln Met Thr Ala Ser Glu Ile Ala Ala Leu Asn Val
                420                 425                 430 gcg aag cgt gag tat cag aaa cag tat atg gac tac tgg cat agc aca   1344
Ala Lys Arg Glu Tyr Gln Lys Gln Tyr Met Asp Tyr Trp His Ser Thr
                435                 440                 445 gcc gag gtg aca ggc acg ggg cgt cct gtt gat gcg cta ttt tgc cca   1392
Ala Glu Val Thr Gly Thr Gly Arg Pro Val Asp Ala Leu Phe Cys Pro
450                 455                 460 ttg gca cct cat gcg gca gtt att ccc ggc gaa ttc aag tct gtg gga   1440
Leu Ala Pro His Ala Ala Val Ile Pro Gly Glu Phe Lys Ser Val Gly
465                 470                 475                 480 tat act gga ttt gtg aat gtg ctt gac tat act agc ctt gcg att cca   1488
Tyr Thr Gly Phe Val Asn Val Leu Asp Tyr Thr Ser Leu Ala Ile Pro
                485                 490                 495 gtc aca ttt gcg gat aag aat atc gat gtg cgc tcg gcc aat gag tct   1536
Val Thr Phe Ala Asp Lys Asn Ile Asp Val Arg Ser Ala Asn Glu Ser
                500                 505                 510 gtg gat gat tct gag cat att cag tgg gat tac gat gcc gag gcc tac   1584
Val Asp Asp Ser Glu His Ile Gln Trp Asp Tyr Asp Ala Glu Ala Tyr
                515                 520                 525 gat ggg gcc ccg gtg gga gtg caa ttg gta ggc agg agg ttg cag gaa   1632
Asp Gly Ala Pro Val Gly Val Gln Leu Val Gly Arg Arg Leu Gln Glu
        530                 535                 540 gag aag atg ttg act cta gct gag tat ttc gaa gaa gag att gct cga   1680
Glu Lys Met Leu Thr Leu Ala Glu Tyr Phe Glu Glu Glu Ile Ala Arg
545                 550                 555                 560 gac acg aaa gag aga gcc tga                                       1701
Asp Thr Lys Glu Arg Ala
```

```
<210> SEQ ID NO 3
<211> LENGTH: 566
<212> TYPE: PRT
<213> ORGANISM: Penicillium chrysogenum

<400> SEQUENCE: 3

Met Thr Gly Thr Ser Trp Lys Leu Lys Gly Glu Ala Lys Arg Gln Ser
1               5                   10                  15

Ile Leu Asn Ala Ile Pro Glu Lys Trp Arg Leu Glu Ser Pro Val Pro
            20                  25                  30

Pro Ala Thr Glu Leu Arg Asp Val Thr Gly Asp Tyr Ile Arg Gln Tyr
        35                  40                  45

Leu Thr Glu His Glu Ile Thr Ile Thr Glu Thr Asp Ala Val Asp Ile
    50                  55                  60

Val Ala Gln Thr Ser Thr Gly Arg Trp Ser Ala Leu Glu Val Thr Glu
65                  70                  75                  80

Ala Phe Cys His Arg Ala Ala Leu Ala His Gln Leu Val Asn Cys Leu
                85                  90                  95

His Glu Val Phe Phe Glu Ala Ala Ile Gln Asp Ala Lys Gln Gln Asp
            100                 105                 110

Glu Tyr Phe Ala Lys His Lys Thr Pro Ile Gly Pro Leu His Gly Leu
        115                 120                 125

Pro Val Ser Leu Lys Asp Gln Phe His Ala Lys Gly Val Glu Thr Thr
    130                 135                 140

Met Gly Tyr Val Gly Trp Ile Asn Thr Phe Gln Gly Arg Gln Asn Asp
145                 150                 155                 160

Pro Arg Ser Gly Thr Glu Glu Ser Glu Leu Val Arg Ala Leu Arg Asn
                165                 170                 175

Leu Gly Ala Val Leu Tyr Cys Lys Thr Ser Val Pro Ala Thr Leu Met
            180                 185                 190

Val Gly Glu Thr Met Asn Asn Ile Ile Gly Tyr Thr Trp Asn Pro Lys
        195                 200                 205

Asn Arg Leu Leu Ser Ser Gly Ser Ser Gly Glu Gly Ala Leu
    210                 215                 220

Ile Ala Leu Arg Gly Ser Pro Ala Gly Phe Gly Thr Asp Ile Gly Gly
225                 230                 235                 240

Ser Val Arg Ile Pro Ala Gly Phe Asn Ser Leu Tyr Gly Ile Arg Pro
                245                 250                 255

Ser Ala Gly Arg Ile Pro Tyr Gln Gly Ala Ala Asn Ser Leu Asp Gly
            260                 265                 270

Gln Gly Ser Ile Leu Ser Val Ile Gly Pro Ile Ala Pro Ser Ala Arg
        275                 280                 285

Ser Leu Thr Phe Leu Phe Lys Ala Val Leu Ser Gln Glu Pro Trp Leu
    290                 295                 300

His Asp Pro Leu Ala Leu Glu Leu Pro Trp Arg Asp Glu Val Val Arg
305                 310                 315                 320

Glu Thr Arg Ala Leu Ile Ala Lys Gly Arg Ala Gly Ser Pro Thr Leu
                325                 330                 335

Ala Phe Gly Ile Met Lys Tyr Asp Gly Met Ala Leu Val His Pro Pro
            340                 345                 350

Ile Ala Arg Gly Leu Arg Ile Val Glu Lys Thr Leu Arg Arg Leu Gly
        355                 360                 365

His Arg Val Val Glu Trp Thr Pro Pro Ser His Ser Ile Ala Asn Glu
```

|  | | | | | | | | | | | | | | |
|---|---|---|---|---|---|---|---|---|---|---|---|---|---|---|
| | | | 370 | | | 375 | | | | 380 | | | | |
| Leu | Leu | Gly | Lys | Ile | Phe | Asn | Met | Asp | Gly | Gly | Ala | Asp | Val | Lys | Tyr |
| 385 | | | | | 390 | | | | | 395 | | | | | 400 |

His Leu Gly Leu Ser Gly Glu Pro Gln Ala Pro Glu Ile Val Cys Asn
                           405                         410                         415

Glu Asn Gly Ile Gln Met Thr Ala Ser Glu Ile Ala Ala Leu Asn Val
                  420                         425                       430

Ala Lys Arg Glu Tyr Gln Lys Gln Tyr Met Asp Tyr Trp His Ser Thr
         435                    440                    445

Ala Glu Val Thr Gly Thr Gly Arg Pro Val Asp Ala Leu Phe Cys Pro
 450                        455                    460

Leu Ala Pro His Ala Ala Val Ile Pro Gly Glu Phe Lys Ser Val Gly
465                  470                    475                    480

Tyr Thr Gly Phe Val Asn Val Leu Asp Tyr Thr Ser Leu Ala Ile Pro
                  485                         490                    495

Val Thr Phe Ala Asp Lys Asn Ile Asp Val Arg Ser Ala Asn Glu Ser
         500                    505                    510

Val Asp Asp Ser Glu His Ile Gln Trp Asp Tyr Asp Ala Glu Ala Tyr
         515                    520                    525

Asp Gly Ala Pro Val Gly Val Gln Leu Val Gly Arg Arg Leu Gln Glu
     530                      535                    540

Glu Lys Met Leu Thr Leu Ala Glu Tyr Phe Glu Glu Ile Ala Arg
545                  550                    555                    560

Asp Thr Lys Glu Arg Ala
                 565

<210> SEQ ID NO 4
<211> LENGTH: 2600
<212> TYPE: DNA
<213> ORGANISM: Penicillium chrysogenum

<400> SEQUENCE: 4

```
aaaaaaggac ggaagtatta ttgttgcacc tcatcatgtc aaggtggcca actcttcaca    60
tcaaccagcc aagtggccga gcagtaactc agccatccaa tcttccttgg tctagtggtg   120
atgatttccg cttgtcatta acaccgataa gcgcgggaga ccggggttcg attccccgag   180
ggagagattt cttttttttt atctctcttt cttatatgtc attattaata tgattttga    240
attaatatgt agtggatagt gtttctaagg agagccaagt tctgtagcaa gatataaagg   300
tgtacaatat cacagcctat cgatattgag taactctgaa cggaatcact ccgcggccca   360
ttccttaacc gaagagaact acatagttct cttccccaca ggtctgaatg aaagcaagt   420
tccgattccg agatagtcat gtagatcaca cagattgtgt gcggggaaat gtgtaggacg   480
aagaactgcc ttgtgtctct ctttcctctt tatatatccc agtttacact ccgaaaccac   540
cagaggtata ccccgcccct gttccatttc aacttcactc ttcaatatga ctcgtaactg   600
ggagagccaa gcgcaaaaag gcagagacat cttgaataat tctattccga aacaatggct   660
tctcccgtc gacaggctgc cgccagtctc acagaaaagt gtggtggact tcccccggaa    720
aagcgggttg ttgagtgagc gcgagctcat catcactgat atgtcggcca cagcactggt   780
gaccgagatg ggcaatggaa aactgagcgc ggaagaggtg atggttgcat tcttgaagag   840
ggcagtgctg ggccatcaac tggtgagacc aagagacccg gctttgtatt ttcagtgttg   900
acaagattgt tagctcaatt tcgcaacgga atttatggca gatgaggcaa tcgctcgcgc   960
caaagagcat gatgagtact acagacgcac tggaaagctg gtggggcctc tggtaagcct  1020
```

-continued

```
atatacctac ccgttgaagt ttataacggc aaggttctaa taaaatagca tggcatacca    1080
atcagcgtca aagaacacat atcaatgaag aaccgaacat gtaacacagg atacgtagct    1140
tggtgagtag atatccacca cgacaaccta cactactgac aagcaataat agggttgata    1200
aagtcaccac ggaagatgcc cttctcctcc aactcttatc caaagccggc gccattttcc    1260
atgtgcggac taaccaaccc cagtcactga tggtacgtcg acacatttca agtagtggt    1320 atatcccata actaacacca tctagcacct gtgctgcagc aataacatca ccggcacaac    1380
attgaaccca ctcaatcgca ctctaagtcc aggcgggtcc tccggcggcg aaggcgcctc    1440
aatgggcttc cgttgcgcac cactagggat tgggagtgat atcggcggat caattcgctg    1500
tcccgcagca tttttgcggtg cgtatggctt ccgcccttcc tcactgagga acccggtaac    1560
agggcttaaa gttgctgctt ctggccagga gacaatccgt ggcgtggtgg gtccgatggc    1620
tagtcgctcg attgaggatc tagagctgtt ccagcgagct gtattggagc aagagccttg    1680
ggatattgag acgtcgctga tgcctgtgcc gtggaagacg gctgatccga agcgggatat    1740
gactgtggct attatgtggg atgatgggta tgtcgtgagc caaatatatg tctgctgaca    1800
gtgtgctaat ccatttttcaa gctgcgtccg cccccatcca cctatcactc gcgctttgcg    1860
acatgccaag gagaagctgg tagcggcagg tgtgaaagtc gtagactgga agccgtataa    1920
gcatcagcat ggttgggaag ttattgtaag tgccaattgt tctctgggca tgcacgctat    1980
tacgctaaca tggtccagcg cgccctatac taccctgatg ctggcagcaa gcaacgtgag    2040
ctacttgccg agtcgggcga gccagcacgc ccactaaccg attgggctct ctcctatggc    2100
caaagcatgc ctctttctca cccggaggca tgggccttgc acgaccagcg cgatatctat    2160
agagacgagt accacgctct gatcaatagt cgtggtgttg actttattct ttccccgaca    2220
tatcctgctg ccgcggcggt gatgggcgag tcgcagtatt ggaattatac tgcaatttgg    2280
aacttggtgg acctgccttc tgtagtgttc ccatcaggaa tcactgtgga tcctaaggta    2340
gatgtgttgt cagaggagga caggaagtat gtccccaggg atgaggttga tgagagggaa    2400
tggcggaagt accagggccc ggagagatac gagggcgcgt cggtgggatt gcagattgct    2460
ggaaggcggt tcaaggacga agagacccta gcggcggcga aggctgtcga ggagattgtt    2520
agcgagaaaa ggcactcgaa aatttgaggg gcttgggaat ggatacagat ttctttgatt    2580
cgttttttaa cattcacata                                                2600
```

<210> SEQ ID NO 5
<211> LENGTH: 1644
<212> TYPE: DNA
<213> ORGANISM: Penicillium chrysogenum
<220> FEATURE:
<221> NAME/KEY: CDS
<222> LOCATION: (1)..(1644)

<400> SEQUENCE: 5

```
atg act cgt aac tgg gag agc caa gcg caa aaa ggc aga gac atc ttg     48
Met Thr Arg Asn Trp Glu Ser Gln Ala Gln Lys Gly Arg Asp Ile Leu
1               5                   10                  15 aat aat tct att ccg aaa caa tgg ctt ctc ccc gtc gac agg ctg ccg     96
Asn Asn Ser Ile Pro Lys Gln Trp Leu Leu Pro Val Asp Arg Leu Pro
            20                  25                  30 cca gtc tca cag aaa agt gtg gtg gac ttc ccc cgg aaa agc ggg ttg    144
Pro Val Ser Gln Lys Ser Val Val Asp Phe Pro Arg Lys Ser Gly Leu
        35                  40                  45 ttg agt gag cgc gag ctc atc atc act gat atg tcg gcc aca gca ctg    192
Leu Ser Glu Arg Glu Leu Ile Ile Thr Asp Met Ser Ala Thr Ala Leu
    50                  55                  60
```

```
gtg acc gag atg ggc aat gga aaa ctg agc gcg gaa gag gtg atg gtt    240
Val Thr Glu Met Gly Asn Gly Lys Leu Ser Ala Glu Glu Val Met Val
 65                  70                  75                  80 gca ttc ttg aag agg gca gtg ctg ggc cat caa ctg ctc aat ttc gca    288
Ala Phe Leu Lys Arg Ala Val Leu Gly His Gln Leu Leu Asn Phe Ala
                 85                  90                  95 acg gaa ttt atg gca gat gag gca atc gct cgc gcc aaa gag cat gat    336
Thr Glu Phe Met Ala Asp Glu Ala Ile Ala Arg Ala Lys Glu His Asp
            100                 105                 110 gag tac tac aga cgc act gga aag ctg gtg ggg cct ctg cat ggc ata    384
Glu Tyr Tyr Arg Arg Thr Gly Lys Leu Val Gly Pro Leu His Gly Ile
        115                 120                 125 cca atc agc gtc aaa gaa cac ata tca atg aag aac cga aca tgt aac    432
Pro Ile Ser Val Lys Glu His Ile Ser Met Lys Asn Arg Thr Cys Asn
130                 135                 140 aca gga tac gta gct tgg gtt gat aaa gtc acc acg gaa gat gcc ctt    480
Thr Gly Tyr Val Ala Trp Val Asp Lys Val Thr Thr Glu Asp Ala Leu
145                 150                 155                 160 ctc ctc caa ctc tta tcc aaa gcc ggc gcc att ttc cat gtg cgg act    528
Leu Leu Gln Leu Leu Ser Lys Ala Gly Ala Ile Phe His Val Arg Thr
                165                 170                 175 aac caa ccc cag tca ctg atg cac ctg tgc tgc agc aat aac atc acc    576
Asn Gln Pro Gln Ser Leu Met His Leu Cys Cys Ser Asn Asn Ile Thr
            180                 185                 190 ggc aca aca ttg aac cca ctc aat cgc act cta agt cca ggc ggg tcc    624
Gly Thr Thr Leu Asn Pro Leu Asn Arg Thr Leu Ser Pro Gly Gly Ser
        195                 200                 205 tcc ggc ggc gaa ggc gcc tca atg ggc ttc cgt tgc gca cca cta ggg    672
Ser Gly Gly Glu Gly Ala Ser Met Gly Phe Arg Cys Ala Pro Leu Gly
    210                 215                 220 att ggg agt gat atc ggc gga tca att cgc tgt ccc gca gca ttt tgc    720
Ile Gly Ser Asp Ile Gly Gly Ser Ile Arg Cys Pro Ala Ala Phe Cys
225                 230                 235                 240 ggt gcg tat ggc ttc cgc cct tcc tca ctg agg aac ccg gta aca ggg    768
Gly Ala Tyr Gly Phe Arg Pro Ser Ser Leu Arg Asn Pro Val Thr Gly
                245                 250                 255 ctt aaa gtt gct gct tct ggc cag gag aca atc cgt ggc gtg gtg ggt    816
Leu Lys Val Ala Ala Ser Gly Gln Glu Thr Ile Arg Gly Val Val Gly
            260                 265                 270 ccg atg gct agt cgc tcg att gag gat cta gag ctg ttc cag cga gct    864
Pro Met Ala Ser Arg Ser Ile Glu Asp Leu Glu Leu Phe Gln Arg Ala
        275                 280                 285 gta ttg gag caa gag cct tgg gat att gag acg tcg ctg atg cct gtg    912
Val Leu Glu Gln Glu Pro Trp Asp Ile Glu Thr Ser Leu Met Pro Val
    290                 295                 300 ccg tgg aag acg gct gat ccg aag cgg gat atg act gtg gct att atg    960
Pro Trp Lys Thr Ala Asp Pro Lys Arg Asp Met Thr Val Ala Ile Met
305                 310                 315                 320 tgg gat gat ggc tgc gtc cgc ccc cat cca cct atc act cgc gct ttg   1008
Trp Asp Asp Gly Cys Val Arg Pro His Pro Pro Ile Thr Arg Ala Leu
                325                 330                 335 cga cat gcc aag gag aag ctg gta gcg gca ggt gtg aaa gtc gta gac   1056
Arg His Ala Lys Glu Lys Leu Val Ala Ala Gly Val Lys Val Val Asp
            340                 345                 350 tgg aag ccg tat aag cat cag cat ggt tgg gaa gtt att cgc gcc cta   1104
Trp Lys Pro Tyr Lys His Gln His Gly Trp Glu Val Ile Arg Ala Leu
        355                 360                 365 tac tac cct gat gct ggc agc aag caa cgt gag cta ctt gcc gag tcg   1152
Tyr Tyr Pro Asp Ala Gly Ser Lys Gln Arg Glu Leu Leu Ala Glu Ser
    370                 375                 380
```

```
ggc gag cca gca cgc cca cta acc gat tgg gct ctc tcc tat ggc caa      1200
Gly Glu Pro Ala Arg Pro Leu Thr Asp Trp Ala Leu Ser Tyr Gly Gln
385                 390                 395                 400 agc atg cct ctt tct cac ccg gag gca tgg gcc ttg cac gac cag cgc      1248
Ser Met Pro Leu Ser His Pro Glu Ala Trp Ala Leu His Asp Gln Arg
            405                 410                 415 gat atc tat aga gac gag tac cac gct ctg atc aat agt cgt ggt gtt      1296
Asp Ile Tyr Arg Asp Glu Tyr His Ala Leu Ile Asn Ser Arg Gly Val
        420                 425                 430 gac ttt att ctt tcc ccg aca tat cct gct gcc gcg gtg atg ggc          1344
Asp Phe Ile Leu Ser Pro Thr Tyr Pro Ala Ala Ala Val Met Gly
    435                 440                 445 gag tcg cag tat tgg aat tat act gca att tgg aac ttg gtg gac ctg      1392
Glu Ser Gln Tyr Trp Asn Tyr Thr Ala Ile Trp Asn Leu Val Asp Leu
450                 455                 460 cct tct gta gtg ttc cca tca gga atc act gtg gat cct aag gta gat      1440
Pro Ser Val Val Phe Pro Ser Gly Ile Thr Val Asp Pro Lys Val Asp
465                 470                 475                 480 gtg ttg tca gag gag gac agg aag tat gtc ccc agg gat gag gtt gat      1488
Val Leu Ser Glu Glu Asp Arg Lys Tyr Val Pro Arg Asp Glu Val Asp
                485                 490                 495 gag agg gaa tgg cgg aag tac cag ggc ccg gag aga tac gag ggc gcg      1536
Glu Arg Glu Trp Arg Lys Tyr Gln Gly Pro Glu Arg Tyr Glu Gly Ala
            500                 505                 510 tcg gtg gga ttg cag att gct gga agg cgg ttc aag gac gaa gag acc      1584
Ser Val Gly Leu Gln Ile Ala Gly Arg Arg Phe Lys Asp Glu Glu Thr
        515                 520                 525 cta gcg gcg gcg aag gct gtc gag gag att gtt agc gag aaa agg cac      1632
Leu Ala Ala Ala Lys Ala Val Glu Glu Ile Val Ser Glu Lys Arg His
    530                 535                 540 tcg aaa att tga                                                      1644
Ser Lys Ile
545
```

<210> SEQ ID NO 6
<211> LENGTH: 547
<212> TYPE: PRT
<213> ORGANISM: Penicillium chrysogenum

<400> SEQUENCE: 6

```
Met Thr Arg Asn Trp Glu Ser Gln Ala Gln Lys Gly Arg Asp Ile Leu
1               5                   10                  15

Asn Asn Ser Ile Pro Lys Gln Trp Leu Leu Pro Val Arg Leu Pro
            20                  25                  30

Pro Val Ser Gln Lys Ser Val Val Asp Phe Pro Arg Lys Ser Gly Leu
        35                  40                  45

Leu Ser Glu Arg Glu Leu Ile Ile Thr Asp Met Ser Ala Thr Ala Leu
    50                  55                  60

Val Thr Glu Met Gly Asn Gly Lys Leu Ser Ala Glu Glu Val Met Val
65                  70                  75                  80

Ala Phe Leu Lys Arg Ala Val Leu Gly His Gln Leu Leu Asn Phe Ala
                85                  90                  95

Thr Glu Phe Met Ala Asp Glu Ala Ile Ala Arg Ala Lys Glu His Asp
            100                 105                 110

Glu Tyr Tyr Arg Arg Thr Gly Lys Leu Val Gly Pro Leu His Gly Ile
        115                 120                 125

Pro Ile Ser Val Lys Glu His Ile Ser Met Lys Asn Arg Thr Cys Asn
    130                 135                 140
```

-continued

```
Thr Gly Tyr Val Ala Trp Val Asp Lys Val Thr Glu Asp Ala Leu
145                 150                 155                 160

Leu Leu Gln Leu Leu Ser Lys Ala Gly Ala Ile Phe His Val Arg Thr
            165                 170                 175

Asn Gln Pro Gln Ser Leu Met His Leu Cys Cys Ser Asn Asn Ile Thr
        180                 185                 190

Gly Thr Thr Leu Asn Pro Leu Asn Arg Thr Leu Ser Pro Gly Gly Ser
    195                 200                 205

Ser Gly Gly Glu Gly Ala Ser Met Gly Phe Arg Cys Ala Pro Leu Gly
210                 215                 220

Ile Gly Ser Asp Ile Gly Gly Ser Ile Arg Cys Pro Ala Ala Phe Cys
225                 230                 235                 240

Gly Ala Tyr Gly Phe Arg Pro Ser Ser Leu Arg Asn Pro Val Thr Gly
                245                 250                 255

Leu Lys Val Ala Ala Ser Gly Gln Glu Thr Ile Arg Gly Val Val Gly
            260                 265                 270

Pro Met Ala Ser Arg Ser Ile Glu Asp Leu Glu Leu Phe Gln Arg Ala
        275                 280                 285

Val Leu Glu Gln Glu Pro Trp Asp Ile Glu Thr Ser Leu Met Pro Val
    290                 295                 300

Pro Trp Lys Thr Ala Asp Pro Lys Arg Asp Met Thr Val Ala Ile Met
305                 310                 315                 320

Trp Asp Asp Gly Cys Val Arg Pro His Pro Pro Ile Thr Arg Ala Leu
                325                 330                 335

Arg His Ala Lys Glu Lys Leu Val Ala Ala Gly Val Lys Val Val Asp
            340                 345                 350

Trp Lys Pro Tyr Lys His Gln His Gly Trp Glu Val Ile Arg Ala Leu
        355                 360                 365

Tyr Tyr Pro Asp Ala Gly Ser Lys Gln Arg Glu Leu Leu Ala Glu Ser
    370                 375                 380

Gly Glu Pro Ala Arg Pro Leu Thr Asp Trp Ala Leu Ser Tyr Gly Gln
385                 390                 395                 400

Ser Met Pro Leu Ser His Pro Glu Ala Trp Ala Leu His Asp Gln Arg
                405                 410                 415

Asp Ile Tyr Arg Asp Glu Tyr His Ala Leu Ile Asn Ser Arg Gly Val
            420                 425                 430

Asp Phe Ile Leu Ser Pro Thr Tyr Pro Ala Ala Ala Val Met Gly
        435                 440                 445

Glu Ser Gln Tyr Trp Asn Tyr Thr Ala Ile Trp Asn Leu Val Asp Leu
    450                 455                 460

Pro Ser Val Val Phe Pro Ser Gly Ile Thr Val Asp Pro Lys Val Asp
465                 470                 475                 480

Val Leu Ser Glu Glu Asp Arg Lys Tyr Val Pro Arg Asp Glu Val Asp
                485                 490                 495

Glu Arg Glu Trp Arg Lys Tyr Gln Gly Pro Glu Arg Tyr Glu Gly Ala
            500                 505                 510

Ser Val Gly Leu Gln Ile Ala Gly Arg Arg Phe Lys Asp Glu Glu Thr
        515                 520                 525

Leu Ala Ala Ala Lys Ala Val Glu Glu Ile Val Ser Glu Lys Arg His
    530                 535                 540

Ser Lys Ile
545

<210> SEQ ID NO 7
```

```
<211> LENGTH: 1227
<212> TYPE: DNA
<213> ORGANISM: Penicillium chrysogenum
<220> FEATURE:
<221> NAME/KEY: CDS
<222> LOCATION: (1)..(1227)

<400> SEQUENCE: 7 atg act cgt aac tgg gag agc caa gcg caa aaa ggc aga gac atc ttg      48
Met Thr Arg Asn Trp Glu Ser Gln Ala Gln Lys Gly Arg Asp Ile Leu
1               5                   10                  15 aat aat tct att ccg aaa caa tgg ctt ctc ccc gtc gac agg ctg ccg      96
Asn Asn Ser Ile Pro Lys Gln Trp Leu Leu Pro Val Asp Arg Leu Pro
            20                  25                  30 cca gtc tca cag aaa agt gtg gtg gac ttc ccc cgg aaa agc ggg ttg     144
Pro Val Ser Gln Lys Ser Val Val Asp Phe Pro Arg Lys Ser Gly Leu
        35                  40                  45 ttg agt gag cgc gag ctc atc atc act gat atg tcg gcc aca gca ctg     192
Leu Ser Glu Arg Glu Leu Ile Ile Thr Asp Met Ser Ala Thr Ala Leu
    50                  55                  60 gtg acc gag atg ggc aat gga aaa ctg agc gcg gaa gag gtg atg gtt     240
Val Thr Glu Met Gly Asn Gly Lys Leu Ser Ala Glu Glu Val Met Val
65                  70                  75                  80 gca ttc ttg aag agg gca gtg ctg ggc cat caa ctg ctc aat ttc gca     288
Ala Phe Leu Lys Arg Ala Val Leu Gly His Gln Leu Leu Asn Phe Ala
                85                  90                  95 acg gaa ttt atg gca gat gag gca atc gct cgc gcc aaa gag cat gat     336
Thr Glu Phe Met Ala Asp Glu Ala Ile Ala Arg Ala Lys Glu His Asp
            100                 105                 110 gag tac tac aga cgc act gga aag ctg gtg ggg cct ctg cat ggc ata     384
Glu Tyr Tyr Arg Arg Thr Gly Lys Leu Val Gly Pro Leu His Gly Ile
        115                 120                 125 cca atc agc gtc aaa gaa cac ata tca atg aag aac cga aca tgt aac     432
Pro Ile Ser Val Lys Glu His Ile Ser Met Lys Asn Arg Thr Cys Asn
    130                 135                 140 aca gga tac gta gct tgg gtt gat aaa gtc acc acg gaa gat gcc ctt     480
Thr Gly Tyr Val Ala Trp Val Asp Lys Val Thr Thr Glu Asp Ala Leu
145                 150                 155                 160 ctc ctc caa ctc tta tcc aaa gcc ggc gcc att ttc cat gtg cgg act     528
Leu Leu Gln Leu Leu Ser Lys Ala Gly Ala Ile Phe His Val Arg Thr
                165                 170                 175 aac caa ccc cag tca ctg atg cac ctg tgc tgc agc aat aac atc acc     576
Asn Gln Pro Gln Ser Leu Met His Leu Cys Cys Ser Asn Asn Ile Thr
            180                 185                 190 ggc aca aca ttg aac cca ctc aat cgc act cta agt cca ggc ggg tcc     624
Gly Thr Thr Leu Asn Pro Leu Asn Arg Thr Leu Ser Pro Gly Gly Ser
        195                 200                 205 tcc ggc ggc gaa ggc gcc tca atg ggc ttc cgt tgc gca cca cta ggg     672
Ser Gly Gly Glu Gly Ala Ser Met Gly Phe Arg Cys Ala Pro Leu Gly
    210                 215                 220 att ggg agt gat atc ggc gga tca att cgc tgt ccc gca gca ttt tgc     720
Ile Gly Ser Asp Ile Gly Gly Ser Ile Arg Cys Pro Ala Ala Phe Cys
225                 230                 235                 240 ggt gcg tat ggc ttc cgc cct tcc tca ctg agg aac ccg gta aca ggg     768
Gly Ala Tyr Gly Phe Arg Pro Ser Ser Leu Arg Asn Pro Val Thr Gly
                245                 250                 255 ctt aaa gtt gct gct tct ggc cag gag aca atc cgt ggc gtg gtg ggt     816
Leu Lys Val Ala Ala Ser Gly Gln Glu Thr Ile Arg Gly Val Val Gly
            260                 265                 270 ccg atg gct agt cgc tcg att gag gat cta gag ctg ttc cag cga gct     864
Pro Met Ala Ser Arg Ser Ile Glu Asp Leu Glu Leu Phe Gln Arg Ala
        275                 280                 285
```

```
gta ttg gag caa gag cct tgg gat att gag acg tcg ctg atg cct gtg       912
Val Leu Glu Gln Glu Pro Trp Asp Ile Glu Thr Ser Leu Met Pro Val
        290                 295                 300 ccg tgg aag acg gct gat ccg aag cgg gat atg act gtg gct att atg       960
Pro Trp Lys Thr Ala Asp Pro Lys Arg Asp Met Thr Val Ala Ile Met
305                 310                 315                 320 tgg gat gat ggc tgc gtc cgc ccc cat cca cct atc act cgc gct ttg      1008
Trp Asp Asp Gly Cys Val Arg Pro His Pro Pro Ile Thr Arg Ala Leu
                325                 330                 335 cga cat gcc aag gag aag ctg gta gcg gca ggt gtg aaa gtc gta gac      1056
Arg His Ala Lys Glu Lys Leu Val Ala Ala Gly Val Lys Val Val Asp
                340                 345                 350 tgg aag ccg tat aag cat cag cat ggt tgg gaa gtt att gta agt gcc      1104
Trp Lys Pro Tyr Lys His Gln His Gly Trp Glu Val Ile Val Ser Ala
                355                 360                 365 aat tgt tct ctg ggc atg cac gct att acg cta aca tgg tcc agc gcg      1152
Asn Cys Ser Leu Gly Met His Ala Ile Thr Leu Thr Trp Ser Ser Ala
370                 375                 380 ccc tat act acc ctg atg ctg gca gca agc aac gtg agc tac ttg ccg      1200
Pro Tyr Thr Thr Leu Met Leu Ala Ala Ser Asn Val Ser Tyr Leu Pro
385                 390                 395                 400 agt cgg gcg agc cag cac gcc cac taa                                   1227
Ser Arg Ala Ser Gln His Ala His
                405

<210> SEQ ID NO 8
<211> LENGTH: 408
<212> TYPE: PRT
<213> ORGANISM: Penicillium chrysogenum

<400> SEQUENCE: 8

Met Thr Arg Asn Trp Glu Ser Gln Ala Gln Lys Gly Arg Asp Ile Leu
1               5                   10                  15

Asn Asn Ser Ile Pro Lys Gln Trp Leu Pro Val Asp Arg Leu Pro
            20                  25                  30

Pro Val Ser Gln Lys Ser Val Val Asp Phe Pro Arg Lys Ser Gly Leu
        35                  40                  45

Leu Ser Glu Arg Glu Leu Ile Ile Thr Asp Met Ser Ala Thr Ala Leu
    50                  55                  60

Val Thr Glu Met Gly Asn Gly Lys Leu Ser Ala Glu Glu Val Met Val
65                  70                  75                  80

Ala Phe Leu Lys Arg Ala Val Leu Gly His Gln Leu Leu Asn Phe Ala
                85                  90                  95

Thr Glu Phe Met Ala Asp Glu Ala Ile Ala Arg Ala Lys Glu His Asp
            100                 105                 110

Glu Tyr Tyr Arg Arg Thr Gly Lys Leu Val Gly Pro Leu His Gly Ile
        115                 120                 125

Pro Ile Ser Val Lys Glu His Ile Ser Met Lys Asn Arg Thr Cys Asn
    130                 135                 140

Thr Gly Tyr Val Ala Trp Val Asp Lys Val Thr Thr Glu Asp Ala Leu
145                 150                 155                 160

Leu Leu Gln Leu Leu Ser Lys Ala Gly Ala Ile Phe His Val Arg Thr
                165                 170                 175

Asn Gln Pro Gln Ser Leu Met His Leu Cys Cys Ser Asn Asn Ile Thr
            180                 185                 190

Gly Thr Thr Leu Asn Pro Leu Asn Arg Thr Leu Ser Pro Gly Gly Ser
        195                 200                 205
```

Ser Gly Gly Glu Gly Ala Ser Met Gly Phe Arg Cys Ala Pro Leu Gly
210                 215                 220

Ile Gly Ser Asp Ile Gly Ser Ile Arg Cys Pro Ala Ala Phe Cys
225                 230                 235                 240

Gly Ala Tyr Gly Phe Arg Pro Ser Ser Leu Arg Asn Pro Val Thr Gly
                245                 250                 255

Leu Lys Val Ala Ala Ser Gly Gln Thr Ile Arg Gly Val Val Gly
                260                 265                 270

Pro Met Ala Ser Arg Ser Ile Glu Asp Leu Glu Leu Phe Gln Arg Ala
            275                 280                 285

Val Leu Glu Gln Glu Pro Trp Asp Ile Glu Thr Ser Leu Met Pro Val
        290                 295                 300

Pro Trp Lys Thr Ala Asp Pro Lys Arg Asp Met Thr Val Ala Ile Met
305                 310                 315                 320

Trp Asp Asp Gly Cys Val Arg Pro His Pro Ile Thr Arg Ala Leu
                325                 330                 335

Arg His Ala Lys Glu Lys Leu Val Ala Ala Gly Val Lys Val Val Asp
            340                 345                 350

Trp Lys Pro Tyr Lys His Gln His Gly Trp Glu Val Ile Val Ser Ala
        355                 360                 365

Asn Cys Ser Leu Gly Met His Ala Ile Thr Leu Thr Trp Ser Ser Ala
370                 375                 380

Pro Tyr Thr Thr Leu Met Leu Ala Ala Ser Asn Val Ser Tyr Leu Pro
385                 390                 395                 400

Ser Arg Ala Ser Gln His Ala His
                405

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: synthetic
      primer

<400> SEQUENCE: 9
cattatatta atatgggcag tcagacctgg g                              31

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: synthetic
      primer

<400> SEQUENCE: 10
cattatcctg caggtcaatt ggattcgtcg atatgacttt c                   41

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: synthetic
      primer

<400> SEQUENCE: 11
cattatatta atatgactgg cacatcctgg aaac                           34

<210> SEQ ID NO 12

```
<211> LENGTH: 37
<212> TYPE: DNA
<213> ORGANISM: Artificial Sequence
<220> FEATURE:
<223> OTHER INFORMATION: Description of Artificial Sequence: synthetic
      primer

<400> SEQUENCE: 12
cattatcctg caggtcaggc tctctctttc gtgtctc                              37

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: synthetic
      primer

<400> SEQUENCE: 13
cattatatta atatgactcg taactgggag agcc                                 34

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: synthetic
      primer

<400> SEQUENCE: 14
cattatcctg caggtcaaat tttcgagtgc cttttctcgc t                         41

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 15
catcaccggc acaacattga acccactc                                       28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: synthetic
      primer

<400> SEQUENCE: 16
ggaccatgtt agcgtaatag cgtgcatgcc                                     30

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 17
catgctttgg ccataggaga gagccc                                         26
```

US 7,951,568 B2

BI-DIRECTIONAL SELECTION MARKERS WITH IMPROVED ACTIVITY

This is a U.S. national-stage application of Int'l Appln. No. PCT/EP2007/053549 under 35 U.S.C. 371, filed Apr. 12, 2007; the entire contents of which are hereby incorporated by reference.

FIELD OF THE INVENTION

The present invention relates to new amdS genes for use in an improved method for the transformation of filamentous fungi for obtaining selection marker gene free recombinant strains.

BACKGROUND OF THE INVENTION

In the field of microbial production of compounds of interest, there is in general a growing desire to use recombinant microorganisms containing as little as possible of foreign DNA. Ideally the transformed microorganism would contain only the desired modifications at the gene(s)-of-interest and as little as possible or remnants of other DNA fragments used during the transformation experiment or during cloning.

Patent applications EP 635,574 and WO 9706261 reveal genes encoding phenotypically selectable markers, which can be removed once the gene(s)-of-interest are stably maintained in the organism. The examples in these patent applications are genes encoding acetamidases, which upon expression in a transformed cell enable the cell to grow on media with acetamide as the sole carbon and/or nitrogen source. This selectable marker has several advantages: it is a dominant but non-antibiotic marker, and it can be used even in fungi with an endogenous amdS gene, like *Aspergillus nidulans* (Tilburn et al., 1983, Gene 26: 205-221). Moreover, this selectable marker is a so-called bi-directional marker, meaning that besides the positive selection for its presence (forward selection) also a reverse selection selecting for the absence of the gene can be applied, using fluoroacetamide (see FIG. 1). This is successfully applied in species from the genera *Aspergillus, Penicillium, Saccharomyces* and *Trichoderma*.

The amdS gene of *Aspergillus nidulans* is successfully used as a selection marker for different fungal species, for instance in *Aspergillus niger* and *Penicillium chrysogenum*. In addition, homologous amdS genes were described, obtained from *Aspergillus niger* for transformation of *Aspergillus niger* and obtained from *Penicillium chrysogenum* for transformation of *Penicillium chrysogenum* (WO 9706261). However, these amdS genes still have a major drawback. The forward selection, e.g. selection for the presence of the selectable marker gene, works, although for one of the genes the present invention will show that this is not the case. The problems become apparent when the reverse selection is applied, e.g. selection for the absence of the selectable marker gene. The most widely used (acet)amidase expression cassette, PgpdA-amdS from *Aspergillus nidulans* can give rise to isolation of false negatives, e.g. isolates which suggest by phenotype that they are devoid of the selection marker as a result of the negative selection protocol, but actually have the selection marker gene or fragments thereof stably maintained in the genome. For some reason they escape the selection pressure. This can be a burden in strain improvement programs where repeated transformations have to be performed, especially in those cases where a high throughput is required. Therefore, a bi-directional selection marker gene that functions 100% correctly in both directions, e.g. the forward and the reverse selection, is not available but is highly desirable.

The present invention surprisingly shows that the reverse selection, i.e. the deletion of an amidase marker gene from microbial strains, works with 100% efficiency when using the amidase encoding genes according to the invention. As a result, sequential modification of industrial production strains is feasible with high efficiency and throughput.

SUMMARY OF THE INVENTION

The present invention provides a polypeptide displaying acetamidase activity and providing a reverse selection on fluoroacetamide. Furthermore, the present invention provides a polynucleotide encoding the above polypeptide and the use of said polynucleotide.

DETAILED DESCRIPTION OF THE INVENTION

In a first aspect, the present invention provides a polypeptide selected from the group consisting of a polypeptide having an amino acid sequence according to SEQ ID NO 3, a polypeptide having an amino acid sequence according to SEQ ID NO 6, a polypeptide having an amino acid that is substantially homologous to the sequence of SEQ ID NO 3 and a polypeptide having an amino acid that is substantially homologous to the sequence of SEQ ID NO 6, the polypeptide displaying acetamidase activity and that providing a reverse selection on fluoroacetamide with an efficiency of at least 95%, preferably at least 96%, more preferably at least 97%, more preferably at least 98%, more preferably at least 99%, most preferably 100%.

The present invention further provides in a second aspect a polynucleotide encoding a polypeptide of the first aspect. In particular, a specific DNA sequence is provided encoding the polypeptide of SEQ ID NO 3, i.e. SEQ ID NO 1 or 2, or encoding the polypeptide of SEQ ID NO 6, i.e. SEQ ID NO 4 or 5. SEQ ID NO 7 is a variant coding sequence derived from the genomic DNA of SEQ ID NO 4, due to an event of alternative splicing, and SEQ ID NO 8 is the protein encoded by the alternative coding sequence. On protein level both polypeptides (i.e. SEQ ID NO 6 and SEQ ID NO 8) are identical up to amino acid 365.

As part of the present invention it is demonstrated that the fluoroacetamide screening using the currently available acetamidase genes is not functioning properly; i.e. screening gives rise to false negative mutants. The amidase genes described by the present invention do not have this problem. The activity of the novel polypeptides encoded by these genes can therefore be characterized as follows:

They enable a forward selection, i.e. provide growth on acetamide as the sole nitrogen source, They enable an efficient reverse selection, i.e. provide resistance to fluoroacetamide with an efficiency of at least 95%, as mentioned above.

In the context of the invention, an efficiency of at least 95% means that at least 95% of the strains resulting from the reverse selection on fluoroacetamide has the amidase gene deleted from the genome. This is typically observed upon further analyzing isolated colonies obtained after selection on standard fluoroacetamide plates containing 32 mM fluoroacetamide, 5 mM urea (as N-source) and 1.1% glucose (see WO 9706261).

A polypeptide having an amino acid sequence that is "substantially homologous" to the sequence of SEQ ID NO 3 and/or 6 is defined as a polypeptide having an amino acid sequence possessing a degree of identity to the specified amino acid sequence of at least 75%, preferably at least 80%, more preferably at least 85%, still more preferably at least 90%, still preferably at least 95%, still more preferably at least 96%, still more preferably at least 97%, still more preferably at least 98% and most preferably at least 99%, the substantially homologous peptide displaying acetamidase activity and providing a reverse selection on fluoroacetamide with an efficiency of at least 95%. A substantially homologous polypeptide may encompass polymorphisms that may exist in cells from different populations or within a population due to natural allelic or intra-strain variation. A substantially homologous polypeptide may further be derived from a fungus other than the fungus where the specified amino acid and/or DNA sequence originates from, or may be encoded by an artificially designed and synthesized DNA sequence. DNA sequences related to the specified DNA sequences and obtained by degeneration of the genetic code are also part of the invention. Homologues may also encompass biologically active fragments of the full-length sequence, for example the polypeptide with an amino acid sequence of SEQ ID NO 8.

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information (URL: ncbi[dot]nlm[dot]nih[dot]gov). The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=−4, and a comparison of both strands.

Substantially homologous polypeptides may contain only conservative substitutions of one or more amino acids of the specified amino acid sequences or substitutions, insertions or deletions of non-essential amino acids. Accordingly, a non-essential amino acid is a residue that can be altered in one of these sequences without substantially altering the biological function. For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

The term "conservative substitution" is intended to mean that a substitution in which the amino acid residue is replaced with an amino acid residue having a similar side chain. These families are known in the art and include amino acids with basic side chains (e.g. lysine, arginine and histidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine tryptophan, histidine).

In one embodiment of the invention, a deteriorated polypeptide of the invention is provided. A "deteriorated polypeptide" of the invention is an acetamidase protein wherein at least the acetamidase activity in the forward selection is decreased. The standard acetamide forward selection provides for a standard assay to measure their activity and thus deteriorated proteins may easily be selected. Deteriorated polypeptides of the invention thus are characterized by the fact that they show less activity in the forward selection (i.e. on acetamide), but they still retain at least 95% efficiency in the reverse selection (i.e. on fluoroacetamide). Such deteriorated enzymes are particular useful if one wants to screen for increased copy numbers after transformation. Introduction of a gene-of-interest (GOI) in filamentous fungi goes via co-transformation; i.e. a mixture of DNA fragments is incubated with the competent cells. This mixture contains at least a gene-fragment encoding a selectable marker (in this case acetamidase). Furthermore, it contains at least one GOI, but this might be extended to several GOI, or even to hundreds of GOI. Transformants are first selected by means of the integration of the selection marker, and are subsequently screened by molecular techniques (i.e. colony PCR or Southern blotting) for the presence of one or more GOI. Depending on the strain, DNA mixture and transformation conditions, 1-50%, or even more than 50%, of the acetamidase positive transformants contain also the GOI. If a high gene copy number of the GOI is desired, one can apply these deteriorated polypeptides of the invention to screen and select for strains with high gene copy numbers of the GOI. As additional copies of a deteriorated amidase will lead to more enzyme molecules and thus more enzyme activity, additional gene copies will lead to better growing isolates that can be selected from a primary transformant. In many of these cases the GOI will also be present in multiple copies. These isolates can thus be screened for additional copies of the GOI too.

Deteriorated polypeptides of the invention may be obtained by randomly introducing mutations along all or part of the amidase coding sequence, such as by saturation mutagenesis, and the resulting mutants can be expressed recombinantly and screened for biological activity. They can also be isolated via error prone PCR or can be produced synthetically.

Alternatively, high copy numbers of a GOI may be obtained using the non-deteriorated amidases as described in SEQ ID NO 3 or 6 or 8, and decreasing the concentration of acetamide or using an N-source having a low bioavailability to the transformant, like acryl amide in agar plates, and then selecting the best growing colonies as the ones with additional gene copies. These isolates can than be screened for additional copies of the GOI too.

The polynucleotide or nucleic acid sequence of the invention may be an isolated polynucleotide of genomic, cDNA, RNA, semi-synthetic, synthetic origin, or any combinations thereof. The term "isolated polynucleotide or nucleic acid sequence" as used herein refers to a polynucleotide or nucleic acid sequence which is essentially free of other nucleic acid sequences, e.g., at least about 20% pure, preferably at least about 40% pure, more preferably at least about 60% pure, even more preferably at least about 80% pure, most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced.

The polypeptides according to the invention and the encoding nucleic acid sequences may be obtained from any eukaryotic cell, preferably from a fungus, more preferably from a filamentous fungus. "Filamentous fungi" include all filamentous forms of the subdivision Eumycota and Oomycota (as defined by Hawksworth et al., 1995, supra). Filamentous fungal strains include, but are not limited to, strains of *Acremonium, Aspergillus, Aureobasidium, Chrysosporium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma*.

In a more preferred embodiment, the nucleic acid sequence encoding a polypeptide of the present invention is obtained from a strain of *Penicillium chrysogenum*.

DNA sequences of the invention may be obtained by hybridization. Nucleic acid molecules corresponding to variants (e.g. natural allelic variants) and homologues of the DNA of the invention can be isolated based on their homology to the nucleic acids disclosed herein using these nucleic acids or a suitable fragment thereof, as a hybridization probe according to standard hybridization techniques, preferably under highly stringent hybridization conditions. Alternatively, one could apply in silico screening through the available genome databases.

"Stringency" of hybridization reactions is readily determinable by one of ordinary skill in the art. For additional details and explanation of stringency of hybridization reactions, see Ausubel et al, Current Protocols in Molecular Biology, Wiley Interscience Publishers, (1995).

The nucleic acid sequence may be isolated by e.g. screening a genomic or cDNA library of the microorganism in question. Once a nucleic acid sequence encoding a polypeptide having an activity according to the invention has been detected with e.g. a probe derived from SEQ ID NO 2 or 5, the sequence may be isolated or cloned by utilizing techniques which are known to those of ordinary skill in the art (see, e.g., J. Sambrook, E. F. Fritsch, and T. Maniatis, 1989, Molecular Cloning, A Laboratory Manual, 2d edition, Cold Spring Harbor, N.Y.).

The cloning of the nucleic acid sequences of the present invention from such (genomic) DNA can also be effected, e.g. by using methods based on polymerase chain reaction (PCR) or antibody screening of expression libraries to detect cloned DNA fragments with shared structural features (See, e.g., Innis et al., 1990, PCR: A Guide to Methods and Application, Academic Press, New York.).

The sequence information as provided herein should not be so narrowly construed as to require inclusion of erroneously identified bases. The specific sequences disclosed herein can be readily used to isolate the complete gene from filamentous fungi, in particular *Penicillium chrysogenum*, which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. The person skilled in the art is capable of identifying such erroneously identified bases and knows how to correct for such errors.

In a third aspect, the present invention discloses a strain comprising the polynucleotide mentioned above in the second aspect. Said strain may be any eukaryotic cell, preferably a fungus, more preferably a filamentous fungus. Filamentous fungal strains include, but are not limited to, strains of *Acremonium, Aspergillus, Aureobasidium, Chrysosporium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, and *Trichoderma*.

In a fourth aspect, the present invention discloses the use of a polynucleotide of the first aspect as a selection marker for selecting transformed host strains. The advantage of the selection marker of the present invention is that it can be easily deleted from the transformed host organism. The deletion of the selection marker is based on dominant selection.

The choice of a host cell in the methods of the present invention will to a large extent depend upon the source of the nucleic acid sequence (gene) of interest encoding a polypeptide. Preferably, the host cell is a eukaryotic cell, more preferably a fungus, most preferably a filamentous fungus. In a preferred embodiment, the filamentous fungal host cell is a cell of a species cited as species from which the polynucleotide of the first aspect may be obtained, examples of which are, but are not limited to, *Aspergillus* species (i.e. *Aspergillus awamori, Aspergillus fumigatus, Aspergillus nidulans, Aspergillus niger, Aspergillus oryzae* or *Aspergillus sojae*), *Chrysosporium* species (i.e. *Chrysosporium lucknowense*) or *Penicillium* species (i.e. *Penicillium chrysogenum*). The host cell may be a wild type filamentous fungus host cell or a variant, a mutant or a genetically modified filamentous fungus host cell. Such modified filamentous fungal host cells include e.g. host cells with reduced protease levels, such as the protease deficient strains as *Aspergillus oryzae* JaL 125 (described in WO 97/35956 or EP 429490); the tripeptidyl-aminopeptidases-deficient *Aspergillus niger* strain as disclosed in WO 96/14404, or host cells with reduced production of the protease transcriptional activator (prtT; as described in WO 01/68864 and US 2004/0191864); host strains like the *Aspergillus oryzae* BECh2, wherein three TAKA amylase genes, two protease genes, as well as the ability to form the metabolites cyclopiazonic acid and kojic acid have been inactivated (BECh2 is described in WO 00/39322); filamentous fungal host cells comprising an elevated unfolded protein response (UPR) compared to the wild type cell to enhance production abilities of a polypeptide of interest (described in US 2004/0186070, US 2001/0034045, WO 01/72783 and WO 2005/123763); host cells with an oxalate deficient phenotype (described in WO 2004/070022); host cells with a reduced expression of an abundant endogenous polypeptide such as a glucoamylase, neutral alpha-amylase A, neutral alpha-amylase B, alpha-1,6-transglucosidase, proteases, cellobiohydrolase and/or oxalic acid hydrolase (as may be obtained by genetic modification according to the techniques described in US 2004/0191864); host cells with an increased efficiency of homologous recombination (having deficient hdfA or hdfB gene as described in WO 2005/095624); *Penicillium* host cells producing adipyl-7-aminodesacetoxycephalosporanic acid and derivatives thereof; and host cells having any possible combination of these modifications.

Nucleic acid constructs, e.g. expression constructs, may contain a gene of interest and the polynucleotide of the invention (selection marker), each operably linked to one or more control sequences, which direct the expression of the encoded polypeptide in a suitable expression host. The nucleic acid constructs may be on one DNA fragment, or, preferably, on separate fragments. Expression will be understood to include any step involved in the production of the polypeptide and may include transcription, post-transcriptional modification, translation, post-translational modification, and secretion. The term nucleic acid construct is synonymous with the term expression vector or cassette when the nucleic acid construct contains all the control sequences required for expression of a coding sequence in a particular host organism. The term "control sequences" is defined herein to include all components, which are necessary or advantageous for the expression of a polypeptide. Each control sequence may be native or foreign to the nucleic acid sequence encoding the polypeptide. Such control sequences may include, but are not limited to, a promoter, a leader, optimal translation initiation sequences (as described in Kozak, 1991, J. Biol. Chem. 266: 19867-19870 and WO 2006/077258), a secretion signal sequence, a pro-peptide sequence, a polyadenylation sequence, a transcription terminator. At a minimum, the control sequences include a promoter, and transcriptional and translational stop signals. The term "operably linked" is defined herein as a configuration in which a control sequence is appropriately placed at a position relative to the coding sequence of the DNA sequence such that the control sequence directs the production of a polypeptide.

The control sequence may include an appropriate promoter sequence containing transcriptional control sequences. The promoter may be any nucleic acid sequence, which shows transcription regulatory activity in the cell including mutant, truncated, and hybrid promoters, and may be obtained from genes encoding extra cellular or intracellular polypeptides. The promoter may be either homologous or heterologous to the cell or to the polypeptide.

Preferred promoters for filamentous fungal cells are known in the art and can be, for example, the glucose-6-phosphate dehyrogenase gpdA promoters, protease promoters such as pepA, pepB, pepC, the glucoamylase glaA promoters, amylase amyA, amyB promoters, the catalase catR or catA promoters, glucose oxidase goxC promoter, beta-galactosidase lacA promoter, alpha-glucosidase aglA promoter, translation elongation factor tefA promoter, xylanase promoters such as xlnA, xlnB, xlnC, xlnD, cellulase promoters such as eglA, eglB, cbhA, promoters of transcriptional regulators such as areA, creA, xlnR, pacC, prtT, etc or any other, and can be found among others at the NCBI website (URL:ncbi[dot]nlm[dot]nih[dot]gov[slash]entrez[slash]).

In a preferred embodiment, the promoter may be derived from a gene, which is highly expressed (defined herein as the mRNA concentration with at least 0.5% (w/w) of the total cellular mRNA). In another preferred embodiment, the promoter may be derived from a gene, which is medium expressed (defined herein as the mRNA concentration with at least 0.01% until 0.5% (w/w) of the total cellular mRNA). In another preferred embodiment, the promoter may be derived from a gene, which is low expressed (defined herein as the mRNA concentration lower than 0.01% (w/w) of the total cellular mRNA).

In an even more preferred embodiment, Micro Array data is used to select genes, and thus promoters of those genes, that have a certain transcriptional level and regulation. In this way one can adapt the gene expression cassettes optimally to the conditions it should function in.

Alternatively, one could clone random DNA fragments in front of the polynucleotides of this invention. Using the acetamide plate assay one can easily screen for active promoters, as these should facilitate growth on acetamide as the sole nitrogen source. These DNA fragments can be derived from many sources, i.e. different species, PCR amplified, synthetically and the like.

The control sequence may also include a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention. Preferred terminators for filamentous fungal cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, trpC gene and *Fusarium oxysporum* trypsin-like protease.

The control sequence may also include a suitable leader sequence, a non-translated region of a mRNA, which is important for translation by the filamentous fungal cell. The leader sequence is operably linked to the 5' terminus of the nucleic acid sequence encoding the polypeptide. Any leader sequence, which is functional in the cell, may be used in the present invention. Preferred leaders for filamentous fungal cells are obtained from the genes encoding *Aspergillus oryzae* TAKA amylase and *Aspergillus nidulans* triose phosphate isomerase and *Aspergillus niger* glaA.

The control sequence may also include a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention. Preferred polyadenylation sequences for filamentous fungal cells are obtained from the genes encoding *Aspergillus oryzae* TAKA amylase, *Aspergillus niger* glucoamylase, *Aspergillus nidulans* anthranilate synthase, *Fusarium oxysporum* trypsin-like protease and *Aspergillus niger* alpha-glucosidase.

For a polypeptide to be secreted, the control sequence may also include a signal peptide-encoding region, which codes for an amino acid sequence linked to the amino terminus of the polypeptide, which can direct the encoded polypeptide into the cell's secretory pathway. The 5'end of the coding sequence of the nucleic acid sequence may inherently contain a signal peptide-coding region naturally linked in translation reading frame with the segment of the coding region, which encodes the secreted polypeptide. Alternatively, the 5'end of the coding sequence may contain a signal peptide-coding region, which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide.

The nucleic acid construct may be an expression vector. The expression vector may be any vector (e.g. a plasmid or virus), which can be conveniently subjected to recombinant DNA procedures and can bring about the expression of the nucleic acid sequence encoding the polypeptide. The choice of the vector will typically depend on the compatibility of the vector with the cell into which the vector is to be introduced. The vectors may be linear or closed circular plasmids.

The vector may be an autonomously replicating vector, i.e. a vector, which exists as an extrachromosomal entity, the replication of which is independent of chromosomal replication, e.g. a plasmid, an extrachromosomal element, a minichromosome, or an artificial chromosome. An autonomously maintained cloning vector for a filamentous fungus may comprise the AMA1-sequence (see e.g. Aleksenko and Clutterbuck (1997), Fungal Genet. Biol. 21: 373-397).

Alternatively, the vector may be one which, when introduced into the cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least at least 0.1 kb, even preferably at least 0.2 kb, more preferably at least 0.5 kb, even more preferably at least 1 kb, most preferably at least 2 kb.

The vector system may be a single vector or plasmid or two or more vectors or plasmids, which together contain the total DNA to be introduced into the genome of the host cell.

The DNA constructs may be used on an episomal vector. However in the present invention the constructs are preferably integrated in the genome of the host strain.

The obtained host cell may be used for producing a compound of interest, for example a primary or secondary metabolite or a polypeptide. A gene of interest may thus encompass a gene encoding a polypeptide involved in a metabolic pathway or may be a gene encoding a polypeptide of interest to be produced.

The present description further uses the term 'introduction' of one or more gene(s)-of-interest (abbreviated as GOI) or fragments thereof. With this is meant an insertion, duplication, deletion, or substitution of a GOI. In general all these alterations can be performed using the polynucleotide of the present invention as a bi-directional selection marker, applying a forward and reverse selection protocol.

The amidase genes disclosed by the present invention not only can be used in the forward selection on acetamide, but perform also very effectively in fluoroacetamide reverse selection procedures to obtain selection marker gene free strains. Due to the fact that a final recombinant strain does not contain the selection marker, the procedure of the present invention can be repeated, so that several alterations suggested above can be combined in one recombinant strain. Surprisingly, it was found that the deletion of an amidase marker gene according to the invention from microbial strains works with a 100% efficiency.

The efficiency of deleting the amidase gene(s) through selection on fluoroacetamide can be increased by flanking the amidase gene by DNA repeats, enabling efficient recombination and subsequent loss of the amidase gene and one of the direct repeats. Alternatively, the amidase genes can be flanked by so-called lox or frt sequences, which upon addition of recombinase enzymes (cre or flp recombinase, respectively), also enables efficient recombination and subsequent loss of the amidase gene and one of the direct repeats. Alternatively, other features can be used to remove the selection marker genes, i.e. restriction enzyme recognition sites.

The invention provides a method for obtaining selection marker gene free recombinant strains comprising the following steps:
(i) transforming a host cell of interest with a polynucleotide comprising a gene of interest (GOI) and/or a polynucleotide comprising a DNA sequence affecting expression of a GOI and with a polynucleotide comprising the selection marker gene according to the invention,
(ii) selecting clones of transformed cells for their capacity to grow on acetamide as the sole nitrogen and/or carbon source,
(iii) effectuating deletion of the selection marker gene from transfected clones by reverse selection on fluoroacetamide.

The present invention further shows that this selection marker gene can be deleted from the chromosomes of the transformed organisms without leaving a trace of DNA used for cloning.

If site-specific (or better locus specific) integration is desired, the sequences used for integration as mentioned under (i) may be surrounded by endogenous DNA fragments homologous to DNA sequences in the host genome. If such a sequence is not present the DNA nevertheless may integrate into the genome. This does not influence the possibility of deletion of the selection marker gene. Alternatively, the sequences of (i) may be surrounded by recognition sites for restriction or recombination enzymes to facilitate efficient integration in step (i) and/or efficient deletion in step (iii).

The present invention further discloses a method for producing a compound of interest comprising:
(i) transforming a host cell of interest with a polynucleotide comprising a gene of interest and/or with a polynucleotide comprising a DNA sequence affecting expression of a gene of interest, and with the polynucleotide comprising the selection marker gene according to the invention,
(ii) selecting clones of transformed cells for their capacity to grow on acetamide as the sole nitrogen and/or carbon source,
(iii) effectuating deletion of the selection marker gene from transformed clones by reverse selection on fluoroacetamide,
(iv) using a reverse selected clone for the production of the compound of interest.

Alternatively, step (iii) can be omitted and the acetamidase containing clone can be used for production of the compound of interest.

The dominant selection and reverse selection method described above can be employed in the development of production strains in various ways:
To introduce a new GOI
The vector used for integration of the amidase gene also contains a gene of interest. The invention thus further enables the introduction of desired foreign or homologous genes or DNA elements in the host organisms of choice using the amidase gene as a selection marker gene. Subsequently, the amidase gene is deleted. Preferably the amidase and the desired genes or DNA elements are introduced site-specifically, where after the amidase gene is deleted.

To introduce multiple GOI sequentially (at predetermined loci)

Specifically, the invention discloses selection marker free organisms containing (site-specifically) introduced genes, which can be used for a new round of transformation. The invention is used for repeated introduction of multiple copies of various genes or a DNA element at a predetermined genomic locus.

To modify transcription levels of a GOI

The method as disclosed by the invention can be used to transform a host cell with a DNA sequence of interest affecting expression of a GOI. For instance, the promoter of a GOI may be mutated or exchanged for a different promoter, thereby altering the regulation and thus expression level of the GOI. Alternatively, one can modify the transcript level of a GOI by introducing an expression construct via co-transformation (see above) which mediates RNA inhibition.

To delete a GOI

The disclosed method can also be used to remove a complete or a certain part of a gene. This is of interest when certain genes coding for proteins that negatively influence production levels of desired proteins or metabolites, again without leaving a marker gene in the genome. Examples are proteases in enzyme production, transcription regulators and competing pathways in metabolite production processes and the like.

To amplify the copy numbers of GOI

The disclosed invention can be used to introduce additional copies of certain genes. This is particularly useful when altering the regulation of these GOI via exchange of the homologous promoter for a strong promoter is not an option.

To introduce site specific mutations in GOI, which alter the kinetics of the protein(s) produced In a fifth aspect, the application of the polypeptides of the present invention can be improved by deleting one or more of the endogenous amidase encoding genes from the genome of the host strain. Although these might be non-functional or non-transcribed genes, deleting them from the genome prevents that they could mutate into active amidases and interfere with the polypeptides from the present invention.

LEGEND TO THE FIGURES

Figure 1:
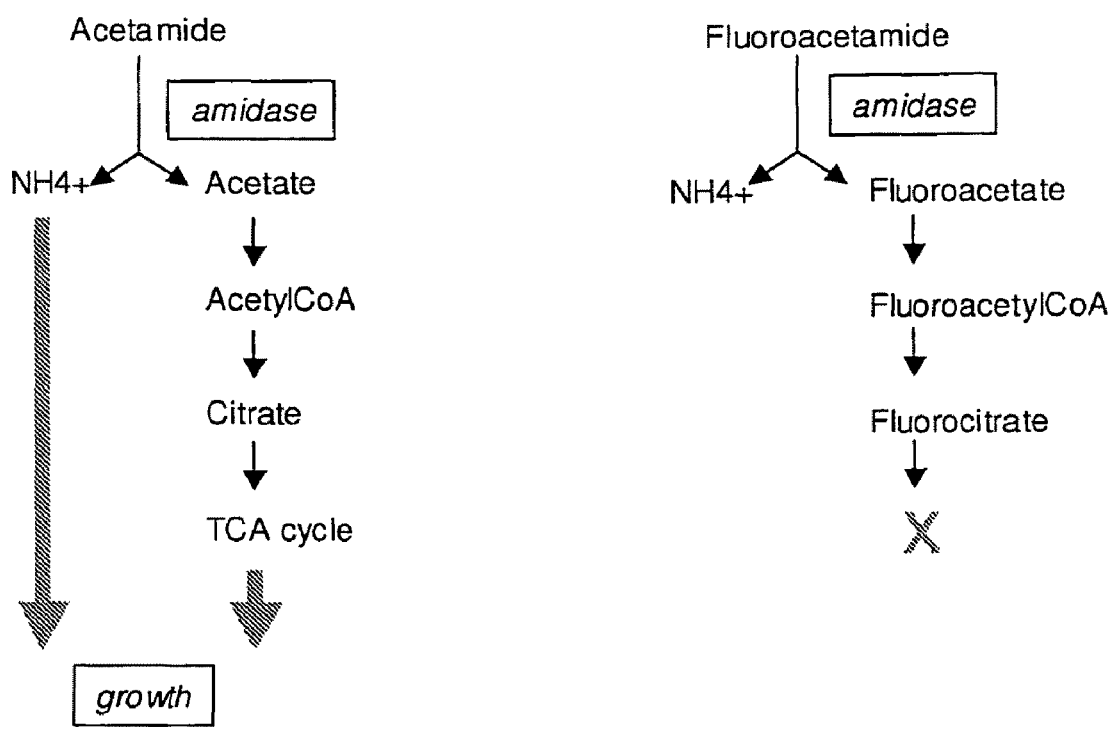
FIG. 1 is a representation of the forward and reverse amidase reactions.
Figure 2:
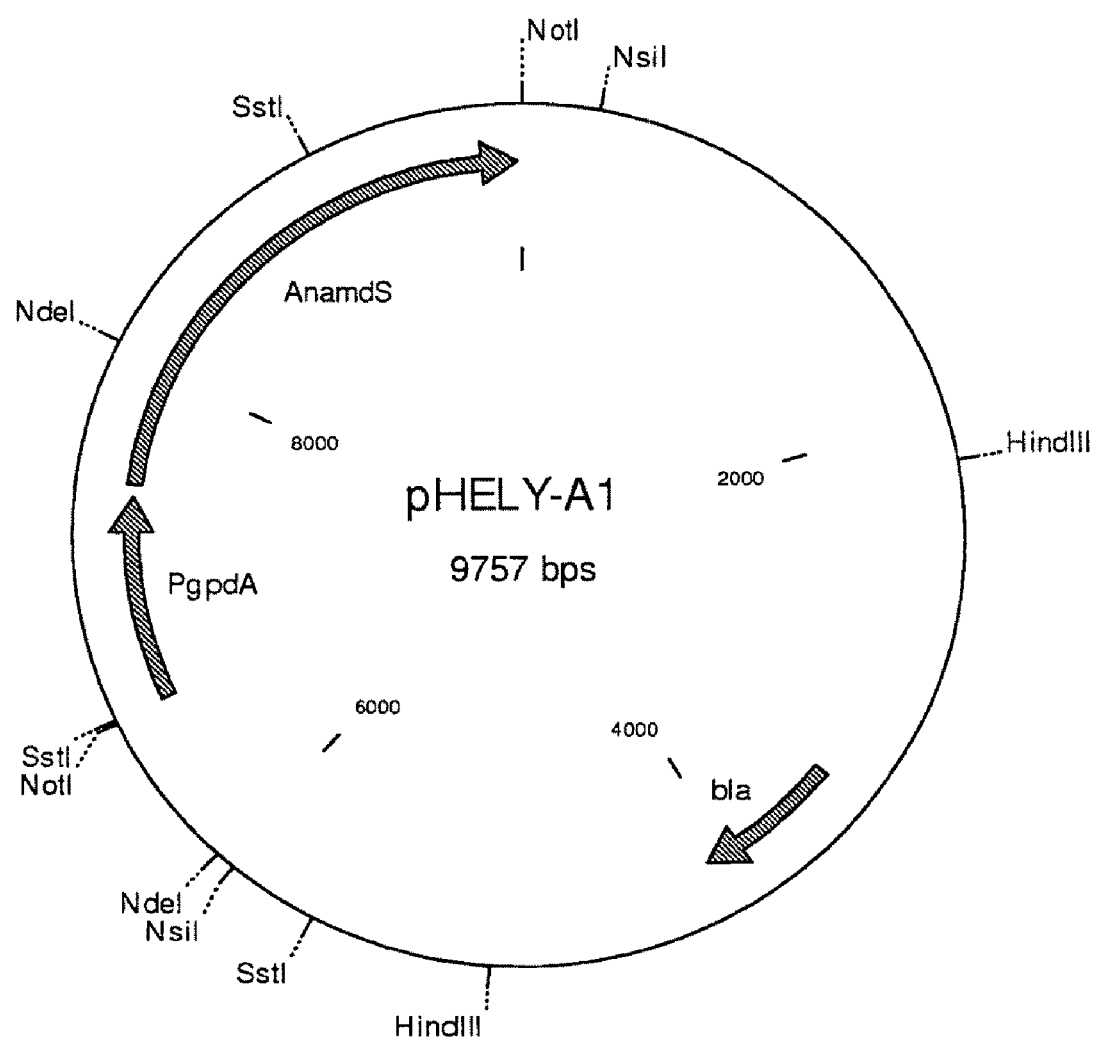
FIG. 2 is a representation of plasmid pHELY-A1, the expression vector for *Aspergillus nidulans* amdS.

FIG. 7 shows the acetamide (left plate) versus fluoroacetamide (right plate) plate selection. A=transformant with *Penicillium chrysogenum* amidase amdA gene; B=transformant with *Penicillium chrysogenum* amidase amdB gene; C=transformant with *Aspergillus nidulans* amdS gene.

FIG. 8 shows the rtPCR on amdB transformants. Panel A is a schematic representation of the 3' part of the gene and the oligonucleotides used. Panel B is the gel-electrophoresis of the amplified fragments (L=kb ladder; 1=transformant 1; 2=transformant 2; 3=transformant 3; 4=transformant 4; 5=control, untransformed strain; a=rtPCR with SEQ ID NO 15 and 16; b=rtPCR with SEQ ID NO 15 and 17).

EXAMPLES

General Methods

In the examples standard molecular techniques have been applied as described in literature (Sambrook et al., 1989, Molecular cloning: a laboratory manual", CSHL press, Cold Spring Harbour, N.Y.), unless stated otherwise.

Example 1

Wild type *Penicillium chrysogenum* cells do not use acetamide as sole N-source *Penicillium chrysogenum* strain Wisconsin 54-1255 (ATCC 28089) was tested for growth on acetamide plates, prepared as described previously (Cantwell C A, Beckmann R J, Dotzlaf J E, Fisher D L, Skatrud P L, Yeh W K, Queener S W (1990) Curr Genet. 17:213-21.) and several growth stages of cells were plated out: spores, mycelium and protoplasts. None of these gave significant growth on acetamide plates, demonstrating that wild type *Penicillium chrysogenum* is not able to use and grow on acetamide.

Example 2

Transformation of *Penicillium chrysogenum* with *Aspergillus nidulans* amdS and Subsequent Reverse Selection Techniques involved in the transfer of DNA to protoplasts of *Penicillium chrysogenum* are well known in the art and are described in many references, including Finkelstein and Ball (eds.), Biotechnology of filamentous fungi, technology and products, Butterworth-Heinemann (1992); Bennett and Lasure (eds.) More Gene Manipulations in fungi, Academic Press (1991); Turner, in: Pühler (ed), Biotechnology, $2^{nd}$ completely revised edition, VHC (1992). The Ca-PEG mediated protoplast transformation is used as described in EP 635,574. pHELY-A1 (described in WO 04106347) was used as expression construct for testing the *Aspergillus nidulans* amdS gene. Two µg of vector was transformed to *Penicillium chrysogenum*. Transformants were selected on media with acetamide as the sole nitrogen source. To secure obtaining stable transformants, first round positives were colony purified on fresh acetamide plates and subsequently transferred to non-selective, rich media (YEPD) to induce sporulation. Afterwards all colonies were again tested on acetamide media. Spores of stable amdS transformants were used to compare growth on acetamide and fluoroacetamide media. For this a spore solution was made in 0.9 mM NaCl and several dilutions were spotted on both media. Although, acetamide positive, and thus amdS positive, in all dilutions there is also growth in the undiluted suspension on fluoroacetamide plates (see FIG. 7), demonstrating that the reverse selection using the *Aspergillus nidulans* amdS is not tight.

Example 3

A Known *Penicillium chrysogenum* amdS is not a Functional Acetamidase

Figure 3:
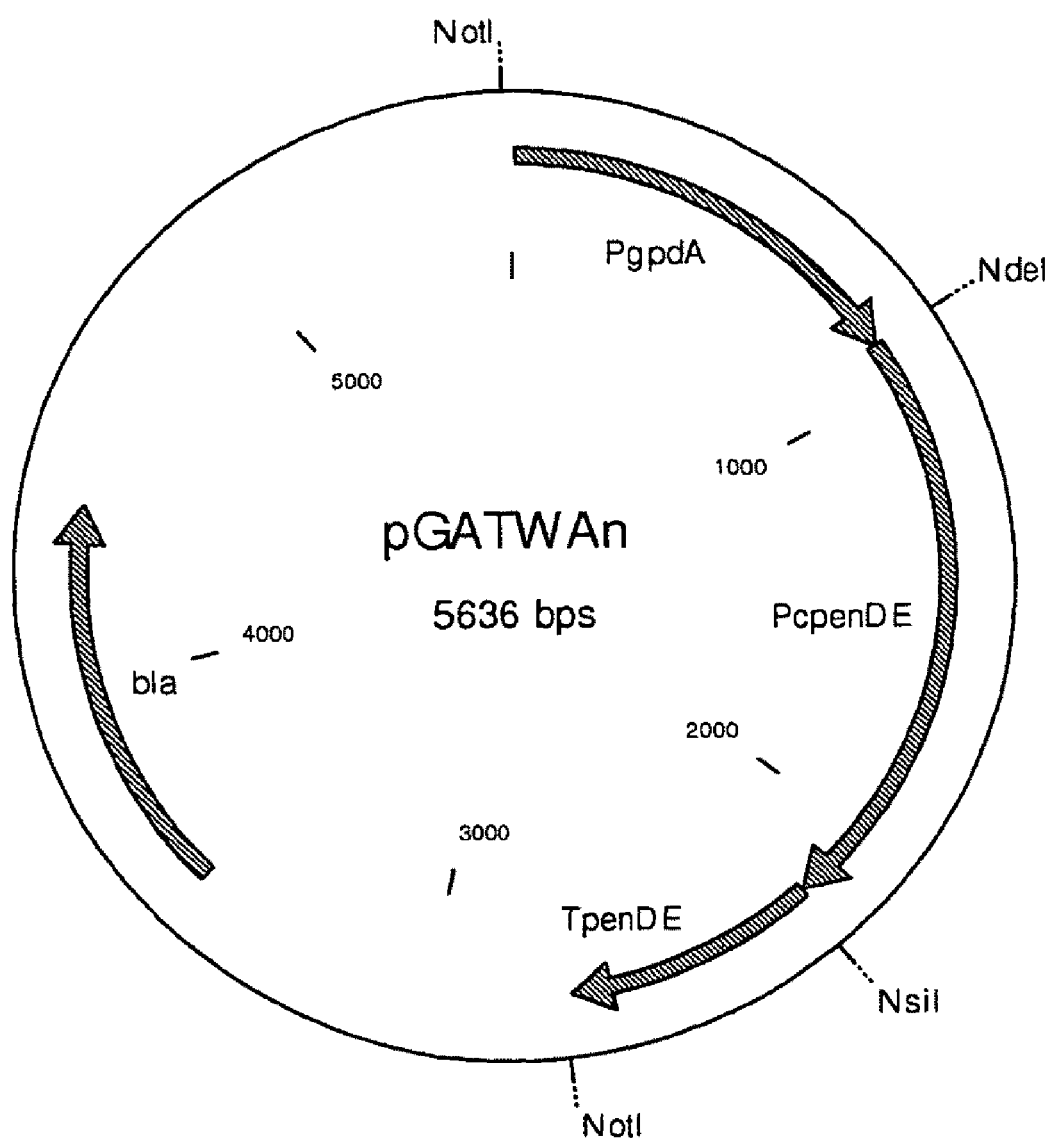
FIG. 3 is a representation of plasmid pGATWAn, a *Penicillium chrysogenum* expression vector.
Figure 4:
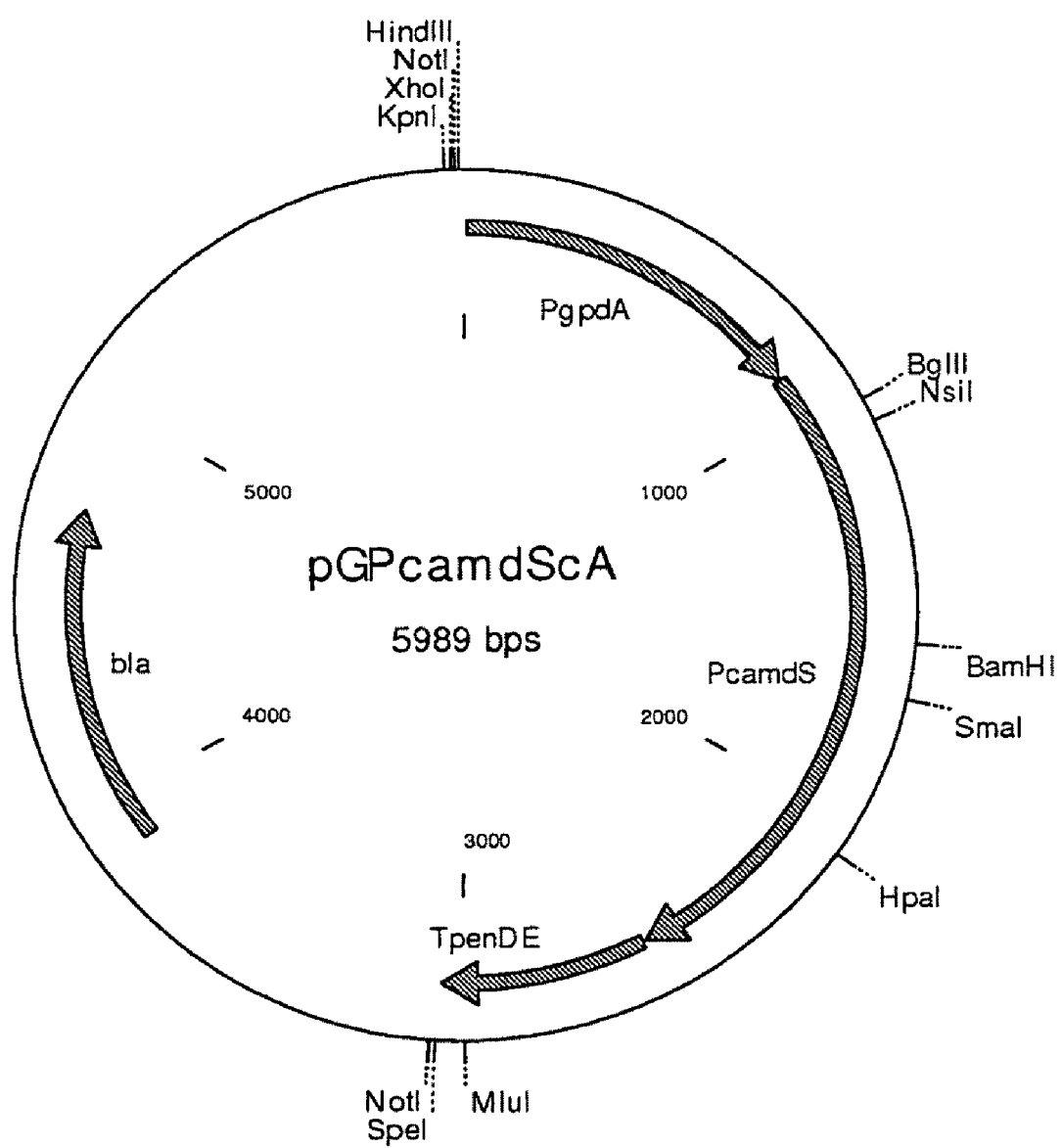
FIG. 4 is a representation of plasmid pGPcamdScA, the expression vector for *Penicillium chrysogenum* amdS (sequence described in EP0758020A2).

An alleged *Penicillium chrysogenum* amdS gene (WO 9706261) was PCR amplified from *Penicillium chrysogenum* DNA using Herculase® Hotstart DNA Polymerase (Stratagene). The oligonucleotides of SEQ ID NO 9 and 10 were used to amplify the ORF. The amplified gene was cloned in pCR®-Blunt II-TOPO® (Invitrogen) and sequence verified before further processing. After digestion with AseI en SbfI, the ORF fragment was cloned in pGATWAn (see FIG. 3) digested with NdeI en NsiI, resulting in the PcamdS expression vector pGPcamdScA (FIG. 4). Vector pGPcamdScA (2 µg) was transformed to *Penicillium chrysogenum* and plated out on media with acetamide as the sole carbon source. No colonies were obtained, demonstrating that the *Penicillium chrysogenum* amdS gene is not functional. Although WO 9706261 discloses this gene sequence with low homology to the *Aspergillus nidulans* amdS gene sequence to be present in the genome of *Penicillium chrysogenum*, we have demonstrated that this gene sequence is not a functional equivalent of the *Aspergillus nidulans* amdS gene and does not enable *Penicillium chrysogenum* to grow on acetamide as the sole N-source.

Example 4

Amidases amdA and amdB of *Penicillium chrysogenum* as Efficient Bi-Directional Selection Marker Genes

Cloning of Genes

Figure 5:
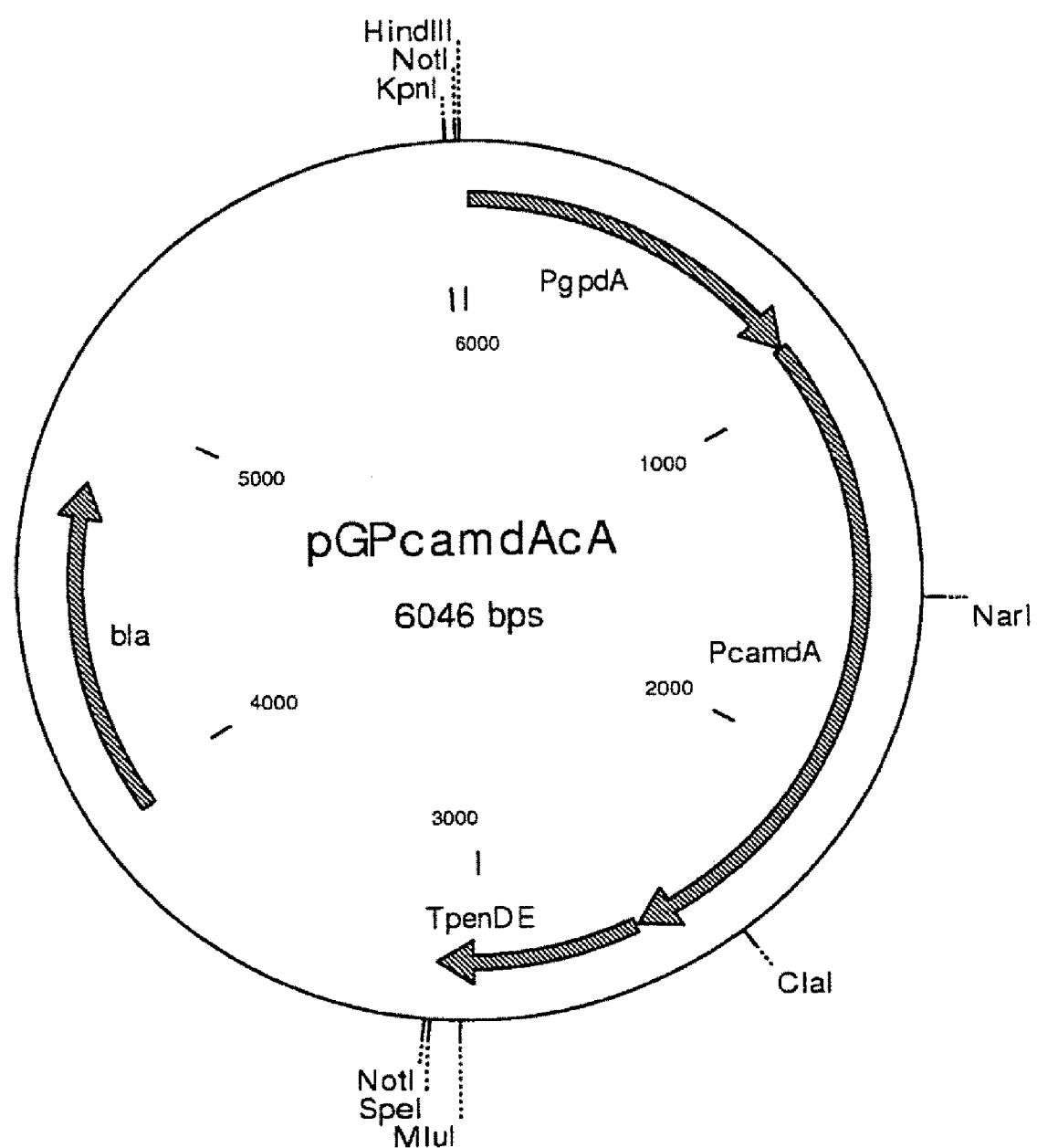
FIG. 5 is a representation of plasmid pGPcamdAcA, the expression vector for *Penicillium chrysogenum* amdA.
Figure 6:
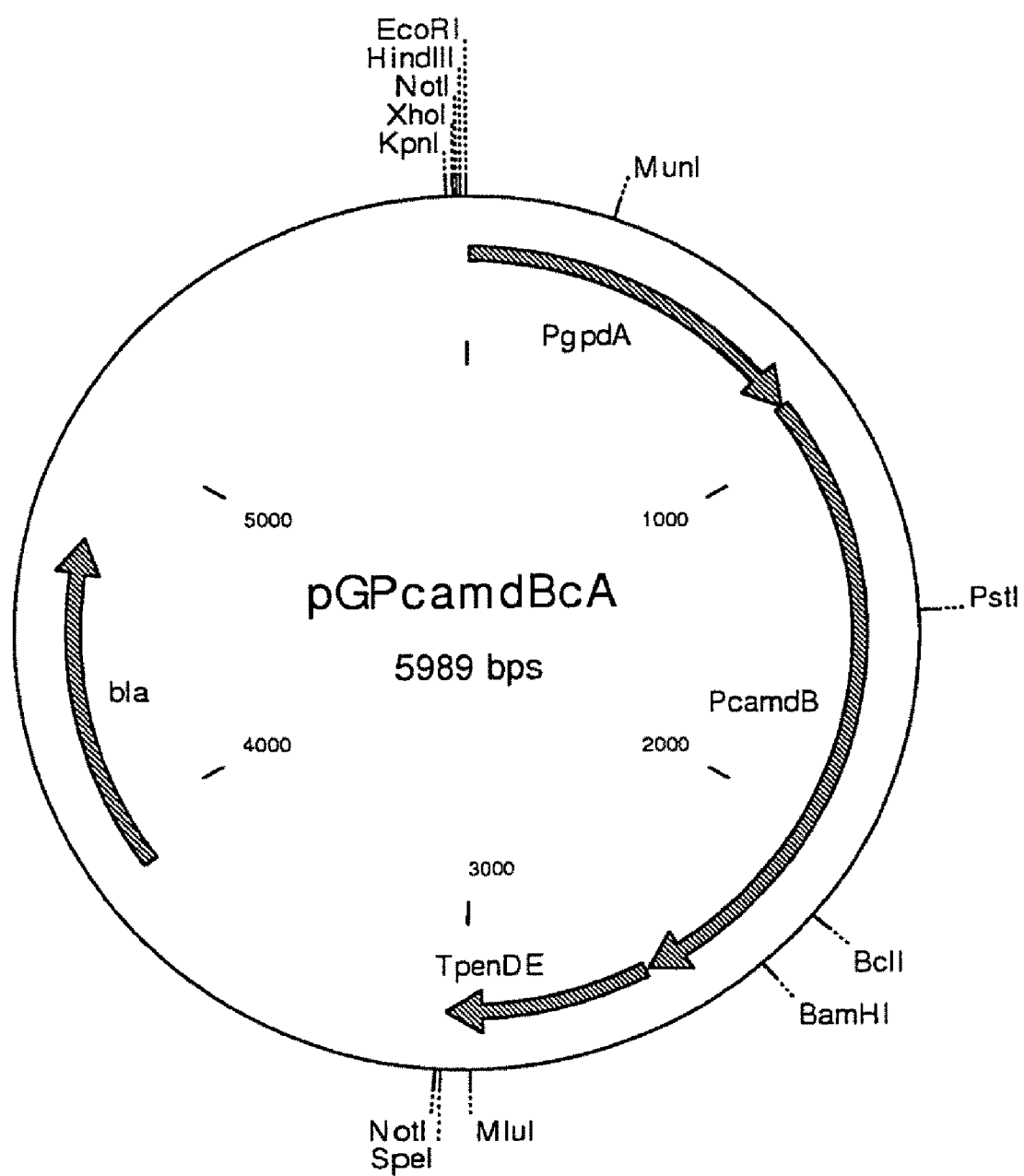
FIG. 6 is a representation of plasmid pGPcamdBcA, the expression vector for *Penicillium chrysogenum* amdB.

Amidase encoding open reading frames amdA and amdB were identified by inspection of the *Penicillium chrysogenum* genome sequence of the Wisconsin54-1255 strain by those skilled in the art. They were PCR amplified from *Penicillium chrysogenum* DNA using Herculase® Hotstart DNA Polymerase (Stratagene). SEQ ID NO 11 and 12 were used to amplify the ORF encoding SEQ ID NO 3; SEQ ID NO 13 and 14 were used to amplify the ORF encoding SEQ ID NO 6. The amplified amidase genes were cloned in pCR®-Blunt II-TOPO® (Invitrogen) and sequence verified before further processing. After digestion with AseI en SbfI, fragments were cloned in pGATWAn digested with NdeI en NsiI, resulting in two new expression vectors pGPcamdAcA and pGPcamdBcA, respectively (see FIGS. 5 and 6).

Acetamide Selection

Two µg of both vectors was transformed to *Penicillium chrysogenum*. Transformants were selected on media with acetamide as the sole nitrogen source. To make sure that stable transformants were obtained, first round positives were colony purified on fresh acetamide plates and subsequently transferred to non-selective, rich media (YEPD) to induce sporulation. Afterwards all colonies were again tested on acetamide media. As stable transformants were obtained, we concluded that both amdA and amdB could function as an acetamidase.

| Gene | Transformants on acetamide |
| --- | --- |
| Pc amdA | ++ |
| Pc amdB | ++ |
| Pc amdS | − |
| An amdS | ++ |

Fluoroacetamide Selection

Spores of the stable amidase transformants were used to compare growth on acetamide and fluoroacetamide media with the *Aspergillus nidulans* amdS (see example 2). For this a spore solution was made in physiological salt (0.9 mM NaCl) and several dilutions were spotted on both media. As demonstrated in FIG. 7, both *Penicillium chrysogenum* amidase genes are supporting growth on acetamide in all dilutions and show no growth in all dilutions on fluoroacetamide plates, demonstrating that the reverse selection using the *Penicillium chrysogenum* amdA and amdB genes is very tight.

| Gene | Growth on fluoroacetamide |
| --- | --- |
| Pc amdA | ---- |
| Pc amdB | ---- |
| Pc amdS | Not tested |
| An amdS | + |

Alternative Splicing of *Penicillium chrysogenum* amdB

The ORF of amdB was amplified from cDNA and after sequencing found to retain one of the predicted introns. Still, this clone was able to give acetamide positive transformants and therefore would be functionally active as an acetamidase. To assess which form of the mRNA was active in the transformants a rtPCR was performed on several transformants. Cells from acetamide plates (inducing conditions) were thereto resuspended in water and RNA was isolated using the StrataPrep® Total RNA Microprep kit (Stratagene). rtPCR was performed with the SuperScript™ III One-Step RT-PCR System (Invitrogen). The results indicate that in all transformants both mRNA variants are present (see FIG. 8).

The invention claimed is:

1. An isolated polypeptide selected from the group consisting of a polypeptide having the amino acid sequence according to SEQ ID NO: 3, and a polypeptide having an amino acid sequence that is at least 95% identical to the sequence of SEQ ID NO: 3, said polypeptide displaying acetamidase activity and providing a reverse selection on fluoracetamide with an efficiency of at least 95%.

* * * * *